(12) United States Patent
Orme et al.

(10) Patent No.: US 6,858,620 B2
(45) Date of Patent: Feb. 22, 2005

(54) CONDENSED PYRIDOINDOLE DERIVATIVES

(75) Inventors: Mark W. Orme, Seattle, WA (US); Jason Scott Sawyer, Indianapolis, IN (US); Alain Claude-Marie Daugan, Les Ulis (FR); Romain Luc Marie Gosmini, Les Ulis (FR); Lisa M. Schultze, Woodinville, WA (US)

(73) Assignee: Lilly ICOS, LLC, Bothell, WA (US)

( * ) Notice: Subject to any disclaimer, the term of this patent is extended or adjusted under 35 U.S.C. 154(b) by 0 days.

(21) Appl. No.: 10/363,528

(22) PCT Filed: Sep. 17, 2001

(86) PCT No.: PCT/US01/42175

§ 371 (c)(1), (2), (4) Date: Mar. 3, 2003

(87) PCT Pub. No.: WO02/28865

PCT Pub. Date: Apr. 11, 2002

(65) Prior Publication Data

US 2004/0082787 A1 Apr. 29, 2004

Related U.S. Application Data

(60) Provisional application No. 60/237,734, filed on Oct. 3, 2000.

(51) Int. Cl.[7] .................. A61K 31/437; C07D 413/04; C07D 417/04
(52) U.S. Cl. .................. 514/287; 546/64; 546/62; 546/70; 514/285
(58) Field of Search .................. 514/287, 285; 546/64, 62, 70

(56) References Cited

FOREIGN PATENT DOCUMENTS

| EP | 0 357 122 | 3/1990 |
| WO | WO 94/10175 | 5/1994 |
| WO | WO 96/32003 | 10/1996 |

OTHER PUBLICATIONS

S. Tanabe, *Chemical Abstracts*, JP 61 0653682 (1986).
N. Kumar et al., *Indian Journal of Chemistry, Section B*: vol. 19B, No. 12, 1087–1088 (1980).
J.S. Madalengoitia et al., *Bioorganic & Medicinal Chemistry*, vol. 5, No. 9, 1807–1815 (1997).
F. Leteurtre et al., *Biochemical Pharmacology*, vol. 49, No. 9, 1283–1290 (1995).
M. L. Lopez Rodriguez et al., *Chem. Pharm. Bull.*, 42(10), 2108–2112 (1994).
M.F. Braña et al., *Synthetic Communications*, 20(12), 1793–1810 (1990).
M. R. Del Giudice et al., *J. Heterocyclic Chem.*, 27, 967–973 (1990).
Y. Saiga et al., *Chem. Pharm. Bull.*, 35(8), 3284–8291 (1987).
T. Hino et al., *Chem. Pharm. Bull.*, 18(2), 384–388 (1970).
H. Faltz et al., *Synlett*, No. 9, 1071–1072 (1997).
M.L. Lopez–Rodriguez et al., *J. Org. Chem.* 59, 1583–1585 (1994).

*Primary Examiner*—Charanjit S. Aulakh
(74) *Attorney, Agent, or Firm*—Marshall, Gerstein & Borun LLP

(57) ABSTRACT

Compounds of general structural formula (I), and use of the compounds or salts or solvates thereof as therapeutic agents, are disclosed

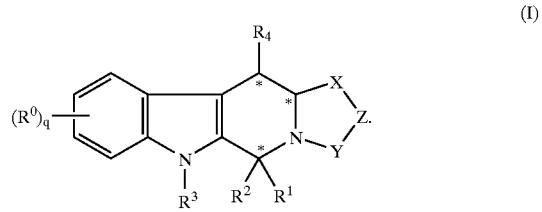

18 Claims, No Drawings

CONDENSED PYRIDOINDOLE DERIVATIVES

CROSS REFERENCE TO RELATED APPLICATIONS

This is the U.S. national phase application of International Application No. PCT/US01/42175, filed Sep. 17, 2001, which claims the benefit of U.S. provisional patent application Ser. No. 60/237,734, filed Oct. 3, 2000.

FIELD AND BACKGROUND OF THE INVENTION

This invention relates to a series of compounds, to methods of preparing the compounds, to pharmaceutical compositions containing the compounds, and to their use as therapeutic agents. In particular, the invention relates to compounds that are potent and selective inhibitors of cyclic guanosine 3',5'-monophosphate specific phosphodiesterase (cGMP-specific PDE), in particular PDE5, and have utility in a variety of therapeutic areas wherein such inhibition is considered beneficial, including the treatment of cardiovascular disorders and erectile dysfunction.

DETAILED DESCRIPTION OF THE INVENTION

The present invention provides compounds of formula (I)

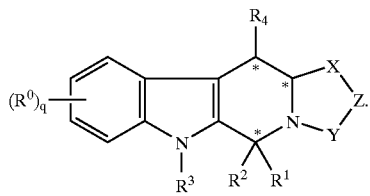

(I)

wherein $R^0$, independently, is selected from the group consisting of halo, $C_{1-6}$alkyl, aryl, heteroaryl, $C_{3-8}$cycloalkyl, $C_{3-8}$heterocycloalkyl, $C_{3-8}$cyclo-alkylQ, $C(=O)R^b$, $OC(=O)R^b$, $C(=O)OR^b$, $C_{1-4}$alkyleneNR$^b$R$^c$, $C_{1-4}$alkyleneHet, $C_{1-4}$alkyleneC(=O)OR$^b$, $C(=O)NR^bSO_2R^d$, $C(=O)C_{1-4}$alkyleneHet, $C(=O)NR^bR^c$, $C(=O)NR^bR^d$, $C(=O)NR^b$—$C_{1-4}$alkyleneOR$^c$, $C(=O)NR^bC_{1-4}$alkyleneHet, $OR^b$, $OC_{1-4}$-alkyleneC(=O)OR$^b$, $OC_{1-4}$alkyleneNR$^b$R$^c$, $OC_{1-4}$alkyleneHet, $OC_{1-4}$alkyleneOR$^b$, $OC_{1-4}$alkyleneNR$^b$C(=O)OR$^c$, $NR^bR^c$, $NR^b$—$C_{1-4}$alkyleneNR$^b$R$^c$, $NR^bC(=O)R^c$, $NR^bC(=O)NR^bR^c$, $N(SO_2C_{1-4}$-alkyl$)_2$, $NR^b(SO_2C_{1-4}$alkyl), nitro, trifluoromethyl, trifluoromethoxy, cyano, $SO_2NR^bR^c$, $SO_2R^b$, $SOR^b$, $SR^b$, and $OSO_2CF_3$;

$R^1$ is selected from the group consisting of optionally substituted aryl, optionally substituted heteroaryl, an optionally substituted $C_{3-8}$cycloalkyl ring, an optionally substituted $C_{3-8}$heterocycloalkyl ring, an optionally substituted bicyclic ring

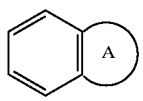

wherein the fused ring A is a 5- or 6-membered ring, saturated or partially or fully unsaturated, and comprises carbon atoms and optionally one to three heteroatoms selected from oxygen, sulfur, and nitrogen, hydrogen, $C_{1-6}$alkyl, aryl$C_{1-3}$alkyl, $C_{1-3}$alkenyl-aryl, halo$C_{1-6}$alkyl, $C_{1-4}$alkyleneC(=O)OR$^b$, $C_{1-4}$alkylene-C(=O)NR$^b$R$^c$, $C_{3-8}$cycloalkyl, $C_{3-8}$cycloalkenyl, $C_{3-8}$hetero-cycloalkenyl, $C_{1-4}$alkyleneHet, $C_{1-4}$alkyleneQR$^b$, $C_{2-6}$-alkenyleneQR$^b$, $C_{1-4}$alkyleneQC$_{1-4}$alkyleneQR$^b$,

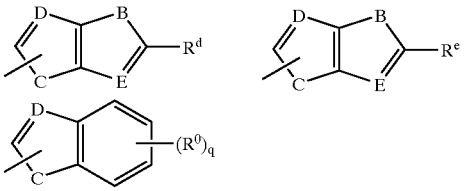

and a spiro substituent having the structure

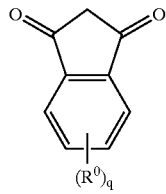

$R^2$ and $R^4$, independently, are selected from the group consisting of hydrogen, $C_{1-6}$alkyl, aryl, heteroaryl, aryl$C_{1-3}$alkyl, $C_{1-3}$alkylenearyl, $C_{1-3}$alkyleneHet, $C_{3-8}$cycloalkyl, and $C_{3-8}$heterocycloalkyl;

$R^3$ is selected from the group consisting of hydrogen, $C_{1-6}$alkyl, $C_{3-8}$cycloalkyl, $C_{3-8}$heterocycloalkyl, $C_{2-6}$alkenyl, $C_{1-3}$alkylenearyl, aryl$C_{1-3}$alkyl, $C(=O)R^b$, aryl, heteroaryl, $C(=O)R^b$, $C(=O)NR^bR^c$, $C(=O)$—NR$^b$R$^d$, $C(=S)NR^bR^c$, $C(=S)NR^bR^d$, $SO_2R^b$, $SO_2NR^bR^c$, $S(=O)R^b$, $S(=O)NR^bR^c$, $C(=O)NR^bC_{1-4}$alkyleneOR$^b$, $C(=O)NR^bC_{1-4}$alkyleneHet, $C(=O)C_{1-4}$alkylenearyl, $C(=O)C_{1-4}$alkyleneheteroaryl, $C_{1-4}$alkylenearyl substituted with one or more of $SO_2NR^bR^c$, $NR^bR^c$, $C(=O)OR^b$, $NR^bSO_2CF_3$, $CN$, $NO_2$, $C(=O)R^b$, $OR^b$, $C_{1-4}$alkyleneNR$^b$R$^c$, and $OC_{1-4}$alkyleneNR$^b$R$^c$, $C_{1-4}$alkyleneheteroaryl, $C_{1-4}$alkyleneHet, $C_{1-4}$alkyleneC(=O) $C_{1-4}$alkylenearyl, $C_{1-4}$alkyleneC(=O) $C_{1-4}$alkyleneheteroaryl, $C_{1-4}$alkyleneC(=O)Het, $C_{1-4}$alkyleneC(=O)NR$^b$R$^c$, $C_{1-4}$alkyleneOR$^b$, $C_{1-4}$alkyleneNR$^b$C(=O)R$^b$, $C_{1-4}$alkylene $OC_{1-4}$alkyleneOR$^b$, $C_{1-4}$alkyleneNR$^b$R$^c$, $C_{1-4}$alkyleneC(=O)OR$^b$, and $C_{1-4}$alkyleneOC$_{1-4}$alkyleneC(=O)OR$^b$;

X and Y, independently, are selected from the group consisting of $C(=O)$, $SO$, $SO_2$, $C(=S)$, $C(R^a)_2$, and $C=C(R^a)_2$;

Z is O, X, or $C(R^a)$ 2, or Z is NR$^d$ when X or Y is SO, SO$_2$, $C(=S)$, $C(R^a)_2$ or $C=C(R^a)_2$;

$R^a$, independently, is selected from the group consisting of hydrogen, $C_{1-10}$alkyl, $C_{2-10}$alkenyl, $C_{2-10}$alkynyl, aryl, heteroaryl, aryl$C_{1-3}$alkyl, $C_{1-3}$alkylenearyl, $C(=O)OR^b$, $C(=O)NR^bR^d$, $C_{1-4}$alkyleneNR$^b$R$^c$, halo, $NO_2$, $CF_3$, $CF_3O$, $OR^b$, $OC(=O)R^b$, $OC_{1-4}$alkyleneC(=O)OR$^b$, $C_{1-4}$alkyleneOC$_{1-4}$alkyleneC(=O)OR$^b$, $C(=O)NR^bSO_2R^d$, $C(=O)C_{1-4}$alkyleneHet, $C_{2-6}$alkenyleneNR$^b$R$^c$, $C(=O)$NR$^a$C$_{1-4}$alkyleneOR$^c$, $C(=O)NR^bC_{1-4}$alkyleneHet, $OC_{2-4}$alkyleneNR$^b$R$^c$, $OC_{1-4}$alkyleneCH(OR$^b$)CH$_2$NR$^b$R$^c$, $OC_{2-4}$alkyleneOR$^b$, $OC_{2-4}$alkyleneNR$^b$C(=O)OR$^c$, $NR^bR^c$, $NR^bC_{1-4}$alkyleneNR$^b$R$^c$, $NR^bC(=O)R^c$, $NR^bC(=O)$NR$^b$R$^c$, $N(SO_2C_{1-4}$-alkyl$)_2$, $NR^b(SO_2C_{1-4}$-alkyl), $SO_2NR^bR^c$, $OSO_2$trifluoromethyl, $C(=O)R^b$, $C_{1-3}$alkyleneOR$^b$, $CN$, and $C_{1-6}$alkyleneC(=O)OR$^b$;

$R^b$ is selected from the group consisting of hydrogen, $C_{1-6}$alkyl, aryl, aryl$C_{1-3}$alkyl, $C_{1-3}$alkylenearyl, heteroaryl, heteroaryl$C_{1-3}$alkyl, and $C_{1-3}$alkyleneheteroaryl;

$R^c$ is selected from the group consisting of hydrogen, $C_{1-6}$alkyl, $C_{3-8}$cycloalkyl, $C_{1-3}$alkyleneN($R^b$)$_2$, aryl, aryl $C_{1-3}$alkyl, $C_{1-3}$alkylenearyl, and heteroaryl;

$R^d$ is selected from the group consisting of hydrogen, $C_{1-6}$alkyl, aryl, heteroaryl, aryl$C_{1-3}$alkyl, heteroaryl $C_{1-3}$alkyl, $C_{1-3}$alkyleneN($R^a$)$_2$, $C_{1-6}$alkylenearyl, $C_{1-6}$alkyleneHet, halo$C_{1-6}$alkyl, $C_{3-8}$cycloalkyl, $C_{3-8}$heterocycloalkyl, $C_{1-3}$alkyleneHet, $C_{1-3}$alkyleneheteroaryl, $C_{1-6}$alkyleneC(=O)OR$^a$, and $C_{1-3}$alkyleneC$_{3-8}$heterocycloalkyl;

or $R^b$ and $R^d$ are taken together to form a 5- or 6-membered ring, optionally containing at least one heteroatom;

$R^e$ is null or is selected from the group consisting of hydrogen, $C_{1-6}$alkyl, aryl, heteroaryl, aryl$C_{1-3}$alkyl, heteroaryl$C_{1-3}$alkyl, $C_{1-3}$alkylenearyl, and $C_{1-3}$alkyleneheteroaryl;

Q is O, S, or NR$^b$;

B is O, S, or NR$^e$;

C is O, S, or NR$^b$;

D is CR$^b$ or N;

E is CR$^b$, C(R$^a$)$_2$, or NR$^e$;

Het represents a 5- or 6-membered heterocyclic ring, saturated or partially or fully unsaturated, containing at least one heteroatom selected from the group consisting of oxygen, nitrogen, and sulfur, and optionally substituted with $C_{1-4}$alkyl or C(=O)OR$^b$;

q is 0, 1, 2, 3, or 4; and pharmaceutically acceptable salts and hydrates thereof.

As used herein, the term "alkyl" includes straight chained and branched hydrocarbon groups containing the indicated number of carbon atoms, typically methyl, ethyl, and straight chain and branched propyl and butyl groups. The hydrocarbon group can contain up to 16 carbon atoms. The term "alkyl" includes "bridged alkyl," i.e., a $C_6$–$C_{16}$ bicyclic or polycyclic hydrocarbon group, for example, norbornyl, adamantyl, bicyclo[2.2.2]octyl, bicyclo[2.2.1]heptyl, bicyclo[3.2.1]octyl, or decahydronaphthyl. The term "cycloalkyl" is defined as a cyclic $C_3$–$C_8$ hydrocarbon group, e.g., cyclopropyl, cyclobutyl, cyclohexyl, and cyclopentyl.

The terms "alkenyl" and "alkynyl" are defined identically as "alkyl," except for containing a carbon-carbon double bond or carbon-carbon triple bond, respectively. "Cycloalkenyl" is defined similarly to cycloalkyl, except a carbon-carbon double bond is present in the ring.

The term "alkylene" refers to an alkyl group having a substituent. For example, the term "$C_{1-3}$alkylenearyl" refers to an alkyl group containing one to three carbon atoms, and substituted with an aryl group. The term "alkenylene" as used herein is similarly defined, and contains the indicated number of carbon atoms and a carbon-carbon double bond, and includes straight chained and branched alkenylene groups, like ethyenylene.

The term "halo" or "halogen" is defined herein to include fluorine, bromine, chlorine, and iodine.

The term "haloalkyl" is defined herein as an alkyl group substituted with one or more halo substituents, either fluoro, chloro, bromo, iodo, or combinations thereof. Similarly, "halocycloalkyl" is defined as a cycloalkyl group having one or more halo substituents.

The term "aryl," alone or in combination, is defined herein as a monocyclic or polycyclic aromatic group, preferably a monocyclic or bicyclic aromatic group, e.g., phenyl or naphthyl. Unless otherwise indicated, an "aryl" group can be unsubstituted or substituted, for example, with one or more, and in particular one to three, halo, alkyl, hydroxy, hydroxyalkyl, alkoxy, alkoxyalkyl, haloalkyl, nitro, amino, alkylamino, acylamino, alkylthio, alkylsulfinyl, and alkylsulfonyl. Exemplary aryl groups include phenyl, naphthyl, tetrahydronaphthyl, 2-chlorophenyl, 3-chlorophenyl, 4-chlorophenyl, 2-methylphenyl, 4-methoxyphenyl, 3-trifluoromethylphenyl, 4-nitrophenyl, and the like. The terms "aryl$C_{1-3}$alkyl" and "heteroaryl$C_{1-3}$alkyl" are defined as an aryl or heteroaryl group having a $C_{1-3}$alkyl substituent.

The term "heteroaryl", is defined herein as a monocyclic or bicyclic ring system containing one or two aromatic rings and containing at least one nitrogen, oxygen, or sulfur atom in an aromatic ring, and which can be unsubstituted or substituted, for example, with one or more, and in particular one to three, substituents, like halo, alkyl, hydroxy, hydroxyalkyl, alkoxy, alkoxyalkyl, haloalkyl, nitro, amino, alkylamino, acylamino, alkylthio, alkylsulfinyl, and alkylsulfonyl. Examples of heteroaryl groups include thienyl, furyl, pyridyl, oxazolyl, quinolyl, isoquinolyl, indolyl, triazolyl, isothiazolyl, isoxazolyl, imidizolyl, benzothiazolyl, pyrazinyl, pyrimidinyl, thiazolyl, and thiadiazolyl.

The term "Het" is defined as monocyclic, bicyclic, and tricyclic groups containing one or more heteroatoms selected from the group consisting of oxygen, nitrogen, and sulfur. A "Het" group also can contain an oxo group (=O) attached to the ring. Nonlimiting examples of Het groups include 1,3-dioxolane, 2-pyrazoline, pyrazolidine, pyrrolidine, piperazine, a pyrroline, 2H-pyran, 4H-pyran, morpholine, thiopholine, piperidine, 1,4-dithiane, and 1,4-dioxane.

The term "hydroxy" is defined as —OH.

The term "alkoxy" is defined as —OR, wherein R is alkyl.

The term "alkoxyalkyl" is defined as an alkyl group wherein a hydrogen has been replaced by an alkoxy group. The term "(alkylthio)alkyl" is defined similarly as alkoxyalkyl, except a sulfur atom, rather than an oxygen atom, is present.

The term "hydroxyalkyl" is defined as a hydroxy group appended to an alkyl group.

The term "amino" is defined as —NH$_2$, and the term "alkylamino" is defined as —NR$_2$, wherein at least one R is alkyl and the second R is alkyl or hydrogen.

The term "acylamino" is defined as RC(=O)N, wherein R is alkyl or aryl.

The term "alkylthio" is defined as —SR, wherein R is alkyl.

The term "alkylsulfinyl" is defined as R—SO$_2$, wherein R is alkyl.

The term "alkylsulfonyl" is defined as R—SO$_3$, wherein R is alkyl.

The term "nitro" is defined as —NO$_2$.

The term "trifluoromethyl" is defined as —CF$_3$.

The term "trifluoromethoxy" is defined as —OCF$_3$.

The term "spiro" as used herein refers to a group having two carbon atoms directly bonded to the carbon atom to which $R^1$ is attached.

The term "cyano" is defined as —CN.

In a preferred embodiment, $R^0$ is selected from the group consisting of aryl, Het, OR$^a$, C(=O)—OR$^a$, $C_{1-4}$alkyleneNR$^a$R$^b$, OC(=O)R$^a$, C(=O)R$^a$, NR$^a$R$^b$, $C_{3-8}$cycloalkyl, $C_{3-8}$cycloalkylQ, C(=O)NR$^a$R$^b$, and C(=O)—NR$^a$R$^c$, or two $R^0$ groups are taken together with the carbon atoms to which they are attached to form a 5 or 6-membered ring, saturated or partially or fully saturated, optionally substituted and optionally containing one or two heteroatoms selected from oxygen, nitrogen, and sulfur.

In a preferred group of compounds of formula (I), $R^1$ is represented by

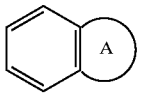

wherein the bicyclic ring can represent, for example, naphthalene or indene, or a heterocycle, such as benzoxazole, benzothiazole, benzisoxazole, benzimidazole, quinoline, indole, benzothiophene, or benzofuran, or

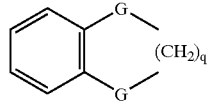

wherein q is an integer 1 or 2, and G, independently, is $C(R^a)_2$, O, S, or $NR^a$. The bicyclic ring comprising the $R^1$ substituent typically is attached to the rest of the molecule by a phenyl ring carbon atom.

In another preferred group of compounds of formula (I), $R^1$ is represented by an optionally substituted bicyclic ring

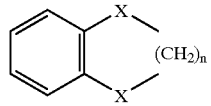

wherein q is 1 or 2, and G, independently, are $C(R^a)_2$ or O. Especially preferred $R^1$ substituents include

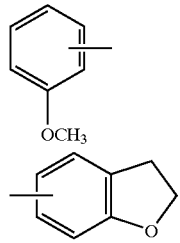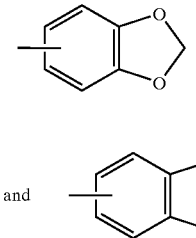

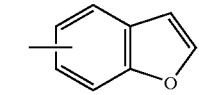

Within this particular group of compounds, nonlimiting examples of substituents for the bicyclic ring include halogen (e.g., chlorine), $C_{1-3}$alkyl (e.g., methyl, ethyl, or i-propyl), $OR^a$ (e.g., methoxy, ethoxy, or hydroxy), $CO_2R^a$, halomethyl or halomethoxy (e.g., trifluoromethyl or trifluoromethoxy), cyano, nitro, and $NR^aR^b$.

In other preferred embodiments, $R^1$ is optionally substituted and selected from the group consisting of $C_{1-4}$alkyleneQ$R^a$, $C_{1-4}$alkyleneQ$C_{1-4}$alkyleneQ$R^a$, $C_{3-8}$cycloalkyl, $C_{3-8}$cycloalkenyl, $C_{1-6}$alkyl,

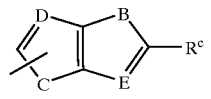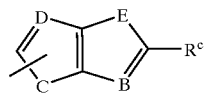

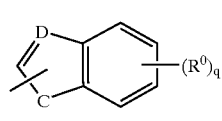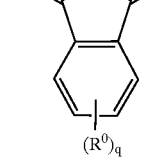

In a more preferred group of compounds of formula (I), $R^1$ is represented by

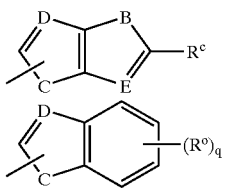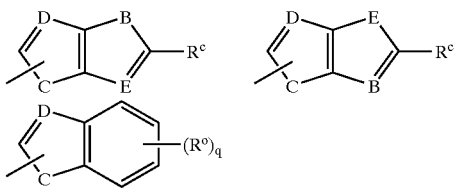

$C_{3-8}$cycloalkyl, $C_{3-8}$cycloalkenyl, $C_{1-6}$alkyl, $C_{1-4}$alkyleneQ$R^a$, and $C_{1-4}$alkyleneQ$C_{1-4}$alkyleneQ$R^a$. A preferred Q is oxygen.

Especially preferred $R^1$ substituents include

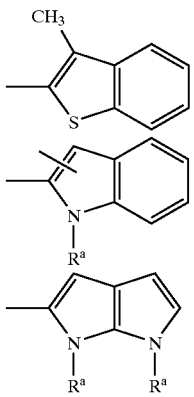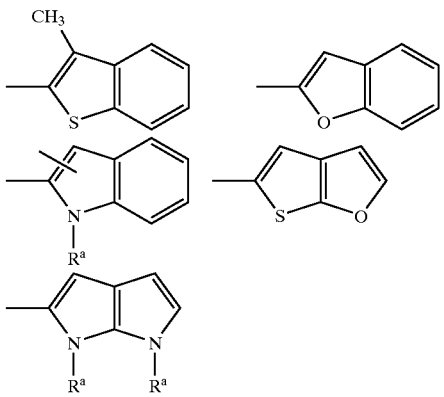

—$CH_2OR^a$, —$CH_2OCH_2OR^a$,

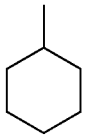 and 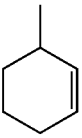

Within this particular group of compounds, preferred $R^a$ substituents include hydrogen, $C_{1-6}$alkyl, and benzyl.

In a preferred embodiment, $R^3$ is selected from the group consisting of aryl, heteroaryl, $OR^b$, $NR^bR^c$, $NR^bR^d$, $C_{1-4}$alkyleneHet, $C_{1-4}$alkyleneheteroaryl, $C_{1-4}$alkylenearyl, $C_{1-4}$alkyleneC(=O)$C_{1-4}$alkylenearyl, $C_{1-4}$alkyleneC(=O)$OR^b$, $C_{1-4}$alkyleneC(=O)$NR^bR^c$, $C_{1-4}$alkyleneC(=O)$NR^bR^d$, $C_{1-4}$alkyleneC(=O)Het, $C_{1-4}$alkyleneNR$^b$R$^c$, $C_{1-4}$alkyleneNR$^b$R$^d$, $C_{1-4}$alkyleneNR$^b$C(=O)$R^b$, and $C_{1-4}$alkyleneOC$_{1-4}$alkyleneOR$^b$.

In more preferred embodiments, $R^1$ is selected from the group consisting of $C_{1-4}$alkyleneheteroaryl, wherein the heteroaryl group is selected from the group consisting of benzimidazole, a triazole, and imidazole; $C_{1-4}$alkyleneHet, wherein Het is selected from the group consisting of piperazine, morpholine, pyrrolidine, pyrrolidone, tetrahydrofuran, piperidine,

 and 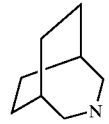

$C_{1-4}$alkyleneC$_6$H$_5$, optionally substituted with one to three groups selected from the group consisting of C(=O)$OR^b$, NR$^b$R$^c$, NR$^b$SO$_2$CF$_3$, SO$_2$NR$^b$R$^c$, CN, OR$^b$, C(=O)$R^b$, $C_{1-4}$alkyleneNR$^b$R$^c$, nitro, OC$_{1-14}$alkylenearyl, and $OC_{1-4}$alkyleneNR$^b$R$^c$; $C_{1-4}$alkyleneC(=O)benzyl; $C_{1-4}$alkyleneC(=O)OR$^b$; $C_{1-4}$alkyleneC(=O)NR$^b$R$^c$; $C_{1-4}$alkyleneC(=O)NR$^b$R$^d$; $C_{1-4}$alkyleneHet; NR$^b$R$^c$; OH; $OC_{1-4}$alkyl; $C_6H_5$; $C_{1-4}$alkyleneNR$^b$R$^c$; $C_{1-4}$alkyleneOR$^b$; $C_{1-4}$alkyleneNHC(=O)R$^b$; and $C_{1-4}$alkylene $OC_{1-4}$alkyleneOR$^b$.

In preferred embodiments, $R^2$ and $R^4$, independently, are hydrogen, $C_{1-6}$alkyl, aryl, or heteroaryl.

In especially preferred embodiments, $R^0$ is selected from the group consisting of halo, methyl, trifluoromethyl, and trifluoromethyl; $R^1$ is selected from the group consisting of

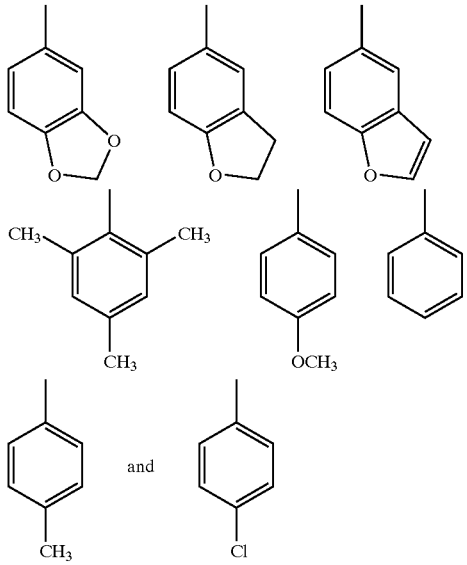

$R^3$ is selected from the group consisting of hydrogen, $C_{1-6}$alkyl, C(=O)NR$^b$R$^d$, and $C_{1-4}$alkyleneHet; $R^2$ and $R^4$ are selected from the group consisting of hydrogen and $C_{1-6}$alkyl; and —X-Z-Y— is selected from the group consisting of

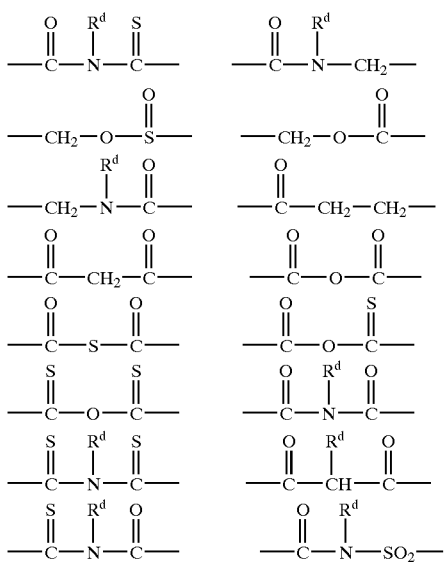

wherein $R^d$ is hydrogen, benzyl, or $C_{1-6}$alkyl.

An especially preferred subclass of compounds within the general scope of formula (I) is represented by compounds of formula (II)

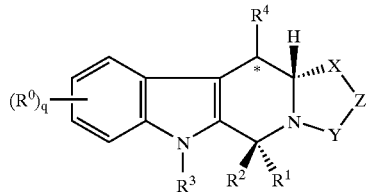

(II)

Compounds of formula (I) can contain one or more asymmetric center, and, therefore, can exist as stereoisomers. The present invention includes both mixtures and separate individual stereoisomers of the compounds of formula (I). Compounds of formula (I) also can exist in tautomeric forms, and the invention includes both mixtures and separate individual tautomers thereof.

Pharmaceutically acceptable salts of the compounds of formula (I) can be acid addition salts formed with pharmaceutically acceptable acids. Examples of suitable salts include, but are not limited to, the hydrochloride, hydrobromide, sulfate, bisulfate, phosphate, hydrogen phosphate, acetate, benzoate, succinate, fumarate, maleate, lactate, citrate, tartrate, gluconate, methanesulfonate, benzenesulfonate, and p-toluenesulfonate salts. The compounds of the formula (I) also can provide pharmaceutically acceptable metal salts, in particular alkali metal salts and alkaline earth metal salts, with bases. Examples include the sodium, potassium, magnesium, and calcium salts.

Compounds of the present invention are potent and selective inhibitors of cGMP-specific PDE5. Thus, compounds of formula (I) are of interest for use in therapy, specifically for the treatment of a variety of conditions where selective inhibition of PDE5 is considered to be beneficial.

Phosphodiesterases (PDEs) catalyze the hydrolysis of cyclic nucleotides, such as cyclic adenosine monophosphate (cAMP) and cyclic guanosine monophosphate (cGMP). The PDEs have been classified into at least seven isoenzyme families and are present in many tissues (J. A. Beavo, *Physiol. Rev.*, 75, p. 725 (1995)).

PDE5 inhibition is a particularly attractive target. A potent and selective inhibitor of PDE5 provides vasodilating, relaxing, and diuretic effects, all of which are beneficial in the treatment of various disease states. Research in this area has led to several classes of inhibitors based on the cGMP basic structure (E. Sybertz et al., *Expert. Opin. Ther. Pat.*, 7, p. 631 (1997)).

The biochemical, physiological, and clinical effects of PDE5 inhibitors therefore suggest their utility in a variety of disease states in which modulation of smooth muscle, renal, hemostatic, inflammatory, and/or endocrine function is desirable. The compounds of formula (I), therefore, have utility in the treatment of a number of disorders, including stable, unstable, and variant (Prinzmetal) angina, hypertension, pulmonary hypertension, congestive heart failure, acute respiratory distress syndrome, acute and chronic renal failure, atherosclerosis, conditions of reduced blood vessel patency (e.g., postpercutaneous transluminal coronary or carotid angioplasty, or post-bypass surgery graft stenosis), peripheral vascular disease, vascular disorders, such as Raynaud's disease, thrombocythemia, inflammatory diseases, stroke, bronchitis, chronic asthma, allergic asthma, allergic rhinitis, glaucoma, osteoporosis, preterm labor, benign prostatic hypertrophy, peptic ulcer, male erectile dysfunction, female sexual dysfunction, and diseases characterized by disorders of gut motility (e.g., irritable bowel syndrome).

An especially important use is the treatment of male erectile dysfunction, which is one form of impotence and is a common medical problem. Impotence can be defined as a lack of power, in the male, to copulate, and can involve an inability to achieve penile erection or ejaculation, or both. The incidence of erectile dysfunction increases with age, with about 50% of men over the age of 40 suffering from some degree of erectile dysfunction.

In addition, a further important use is the treatment of female arousal disorder. Female arousal disorders are defined as a recurrent inability to attain or maintain an adequate lubrication/swelling response of sexual excitement until completion of sexual activity. The arousal response consists of vasocongestion in the pelvis, vaginal lubrication, and expansion and swelling of external genitalia.

It is envisioned, therefore, that compounds of formula (I) are useful in the treatment of male erectile dysfunction and female arousal disorder. Thus, the present invention concerns the use of compounds of formula (I), or a pharmaceutically acceptable salt thereof, or a pharmaceutical composition containing either entity, for the manufacture of a medicament for the curative or prophylactic treatment of erectile dysfunction in a male animal and arousal disorder in a female animal, including humans.

The term "treatment" includes preventing, lowering, stopping, or reversing the progression or severity of the condition or symptoms being treated. As such, the term "treatment" includes both medical therapeutic and/or prophylactic administration, as appropriate.

It also is understood that "a compound of formula (I)," or a physiologically acceptable salt or solvate thereof, can be administered as the neat compound, or as a pharmaceutical composition containing either entity.

Although the compounds of the invention are envisioned primarily for the treatment of sexual dysfunction in humans, such as male erectile dysfunction and female arousal disorder, they also can be used for the treatment of other disease states.

A further aspect of the present invention, therefore, is providing a compound of formula (I) for use in the treatment of stable, unstable, and variant (Prinzmetal) angina, hypertension, pulmonary hypertension, chronic obstructive pulmonary disease, congestive heart failure, acute respiratory distress syndrome, acute and chronic renal failure, atherosclerosis, conditions of reduced blood vessel patency (e.g., post-PTCA or post-bypass graft stenosis), peripheral vascular disease, vascular disorders such as Raynaud's disease, thrombocythemia, inflammatory diseases, prophylaxis of myocardial infarction, prophylaxis of stroke, stroke, bronchitis, chronic asthma, allergic asthma, allergic rhinitis, glaucoma, osteoporosis, preterm labor, benign prostatic hypertrophy, male and female erectile dysfunction, or diseases characterized by disorders of gut motility (e.g., IBS).

According to another aspect of the present invention, there is provided the use of a compound of formula (I) for the manufacture of a medicament for the treatment of the above-noted conditions and disorders.

In a further aspect, the present invention provides a method of treating the above-noted conditions and disorders in a human or nonhuman animal body which comprises administering to said body a therapeutically effective amount of a compound of formula (I).

Compounds of the invention can be administered by any suitable route, for example by oral, buccal, inhalation, sublingual, rectal, vaginal, transurethral, nasal, topical, percutaneous, i.e., transdermal, or parenteral (including intravenous, intramuscular, subcutaneous, and intracoronary) administration. Parenteral administration can be accomplished using a needle and syringe, or using a high pressure technique, like POWDERJECT™.

Oral administration of a compound of the invention is the preferred route. Oral administration is the most convenient and avoids the disadvantages associated with other routes of administration. For patients suffering from a swallowing disorder or from impairment of drug absorption after oral administration, the drug can be administered parenterally, e.g., sublingually or buccally.

Compounds and pharmaceutical compositions suitable for use in the present invention include those wherein the active ingredient is administered in an effective amount to achieve its intended purpose. More specifically, a "therapeutically effective amount" means an amount effective to prevent development of, or to alleviate the existing symptoms of, the subject being treated. Determination of the effective amounts is well within the capability of those skilled in the art, especially in light of the detailed disclosure provided herein.

A "therapeutically effective dose" refers to that amount of the compound that results in achieving the desired effect. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, which is expressed as the ratio between $LD_{50}$ and $ED_{50}$. Compounds which exhibit high therapeutic indices are preferred. The data obtained from such data can be used in formulating a dosage range for use in humans. The dosage of such compounds preferably lies within a range of circulating concentrations that include the $ED_{50}$ with little or no toxicity. The dosage can vary within this range depending upon the dosage form employed, and the route of administration utilized.

The exact formulation, route of administration, and dosage can be chosen by the individual physician in view of the patient's condition. Dosage amount and interval can be adjusted individually to provide plasma levels of the active moiety which are sufficient to maintain the therapeutic effects.

The amount of composition administered is dependent on the subject being treated, on the subject's weight, the severity of the affliction, the manner of administration, and the judgment of the prescribing physician.

Specifically, for administration to a human in the curative or prophylactic treatment of the conditions and disorders identified above, oral dosages of a compound of formula (I) generally are about 0.5 to about 1000 mg daily for an average adult patient (70 kg). Thus, for a typical adult patient, individual tablets or capsules contain 0.2 to 500 mg of active compound, in a suitable pharmaceutically acceptable vehicle or carrier, for administration in single or multiple doses, once or several times per day. Dosages for intravenous, buccal, or sublingual administration typically are 0.1 to 500 mg per single dose as required. In practice, the physician determines the actual dosing regimen which is most suitable for an individual patient, and the dosage varies with the age, weight, and response of the particular patient. The above dosages are exemplary of the average case, but there can be individual instances in which higher or lower dosages are merited, and such are within the scope of this invention.

For human use, a compound of the formula (I) can be administered alone, but generally is administered in admixture with a pharmaceutical carrier selected with regard to the intended route of administration and standard pharmaceutical practice. Pharmaceutical compositions for use in accordance with the present invention thus can be formulated in a conventional manner using one or more physiologically acceptable carriers comprising excipients and auxiliaries that facilitate processing of compounds of formula (I) into preparations which can be used pharmaceutically.

These pharmaceutical compositions can be manufactured in a conventional manner, e.g., by conventional mixing, dissolving, granulating, dragee-making, levigating, emulsifying, encapsulating, entrapping, or lyophilizing processes. Proper formulation is dependent upon the route of administration chosen. When a therapeutically effective amount of a compound of the present invention is administered orally, the composition typically is in the form of a tablet, capsule, powder, solution, or elixir. When administered in tablet form, the composition can additionally contain a solid carrier, such as a gelatin or an adjuvant. The tablet, capsule, and powder contain about 5 to about 95% compound of the present invention, and preferably from about 25 to about 90% compound of the present invention. When administered in liquid form, a liquid carrier such as water, petroleum, or oils of animal or plant origin can be added. The liquid form of the composition can further contain physiological saline solution, dextrose or other saccharide solutions, or glycols. When administered in liquid form, the composition contains about 0.5 to about 90% by weight of a compound of the present invention, and preferably about 1 to about 50% of a compound of the present invention.

When a therapeutically effective amount of a compound of the present invention is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, in addition to a compound of the present invention, an isotonic vehicle.

For oral administration, the compounds can be formulated readily by combining a compound of formula (I) with pharmaceutically acceptable carriers well known in the art. Such carriers enable the present compounds to be formulated as tablets, pills, dragees, capsules, liquids, gels, syrups, slurries, suspensions and the like, for oral ingestion by a patient to be treated. Pharmaceutical preparations for oral use can be obtained by adding a compound of formula (I) with a solid excipient, optionally grinding a resulting mixture, and processing the mixture of granules, after adding suitable auxiliaries, if desired, to obtain tablets or dragee cores. Suitable excipients include, for example, fillers and cellulose preparations. If desired, disintegrating agents can be added.

For administration by inhalation, compounds of the present invention are conveniently delivered in the form of an aerosol spray presentation from pressurized packs or a nebulizer, with the use of a suitable propellant. In the case of a pressurized aerosol, the dosage unit can be determined by providing a valve to deliver a metered amount. Capsules and cartridges of, e.g., gelatin, for use in an inhaler or insufflator can be formulated containing a powder mix of the compound and a suitable powder base such as lactose or starch.

The compounds can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

Compounds of the present invention also can be formulated in rectal compositions, such as suppositories or retention enemas, e.g., containing conventional suppository bases. In addition to the formulations described previously, the compounds also can be formulated as a depot preparation. Such long-acting formulations can be administered by implantation (for example, subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

Many of the compounds of the present invention can be provided as salts with pharmaceutically compatible counterions. Such pharmaceutically acceptable base addition salts are those salts that retain the biological effectiveness and properties of the free acids, and that are obtained by reaction with suitable inorganic or organic bases.

In particular, a compound of formula (I) can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. A compound also can be injected parenterally, for example, intravenously, intramuscularly, subcutaneously, or intracoronarily. For parenteral administration, the compound is best used in the form of a sterile aqueous solution which can contain other substances, for example, salts, or monosaccharides, such as mannitol or glucose, to make the solution isotonic with blood.

For veterinary use, a compound of formula (I) or a nontoxic salt thereof, is administered as a suitably acceptable formulation in accordance with normal veterinary practice. The veterinarian can readily determine the dosing regimen and route of administration that is most appropriate for a particular animal.

Thus, the invention provides in a further aspect a pharmaceutical composition comprising a compound of the formula (I), together with a pharmaceutically acceptable diluent or carrier therefor. There is further provided by the present invention a process of preparing a pharmaceutical composition comprising a compound of formula (I), which process comprises mixing a compound of formula (I), together with a pharmaceutically acceptable diluent or carrier therefor.

In a particular embodiment, the invention includes a pharmaceutical composition for the curative or prophylactic treatment of erectile dysfunction in a male animal, or arousal disorder in a female animal, including humans, comprising a compound of formula (I) or a pharmaceutically acceptable salt thereof, together with a pharmaceutically acceptable diluent or carrier.

Compounds of formula (I) can be prepared by any suitable method known in the art, or by the following processes which form part of the present invention. In the methods below, $R^0$, $R^1$, $R^2$, $R^3$, and $R^4$ are as defined in structural formula (I) above. In particular, Daugan U.S. Pat. No. 5,859,006, incorporated herein by reference, discloses preparation of a compound of structural formula (III).

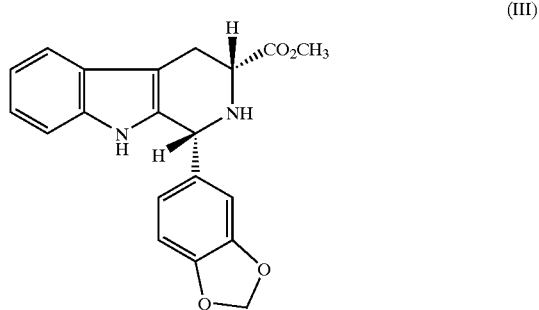

(III)

In short, the compound of structural formula (III), i.e., the cis-isomer of Intermediates 1 and 2 of Daugan U.S. Pat. No. 5,859,006 was prepared according to the following reaction scheme:

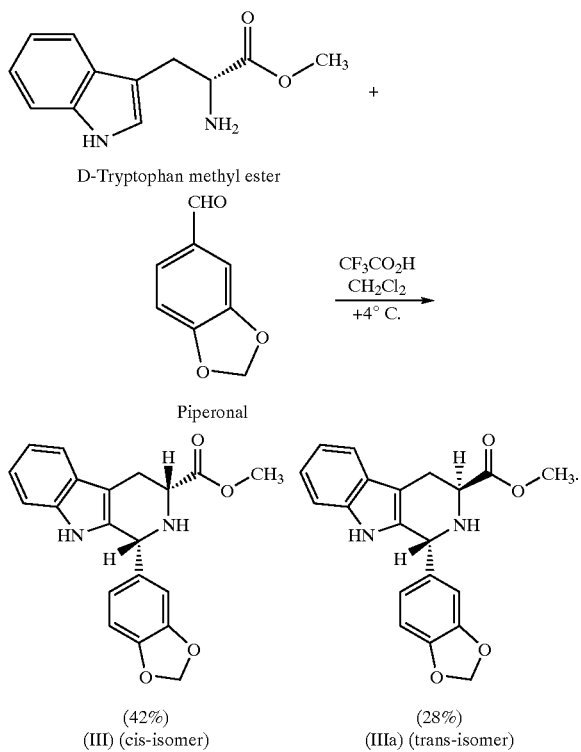

A compound of structural formula (I) is prepared similarly by reacting a tryptophan ester, or a tryptophan ester substituted with suitable $R^0$ substituents, with a suitable aldehyde to provide the desired $R^1$ substituent. The resulting product then is hydrolyzed to the carboxylic acid, and cyclized by reaction with a suitable cyclizing agent like phosgene, thiocarbonyl diimidazole, or thiophosgene, for example, to provide a compound of structural formula (I).

In the synthesis of compounds of structural formula (I), protecting compounds and protecting groups, like benzyl chloroformate and trichloroethyl chloroformate, which are well known to persons skilled in the art, can be used. Such protecting groups are disclosed, for example, in T. W. Greene et al. "Protective Groups in Organic Synthesis, Third Edition," John Wiley and Sons, Inc., NY, N.Y. (1999). The structure of a compound of structural formula (I) can be varied by using an appropriate aldehyde to change the identity of $R^1$, or by using a halo or alkyl phenyl-substituted tryptophan ester.

Compounds of formula (I) can be converted to other compounds of formula (I). Thus, for example, when a compound contains a substituted aromatic ring, it is possible to prepare another suitably substituted compound of formula (I). Examples of appropriate interconversions include, but are not limited to, $OR^b$ to hydroxy by suitable means (e.g., using an agent such as $SnCl_2$ or a palladium catalyst, such as palladium-on-carbon, or amino to substituted amino, such as alkylamine, using standard acylating or sulfonylating conditions.

Compounds of formula (I) can be prepared by the method above as individual stereoisomers from the appropriate stereoisomer of formula (III) or as a racemic mixture from the appropriate racemic compound of formula (III). Individual stereoisomers of the compounds of the invention can be prepared from racemates by resolution using methods known in the art for the separation of racemic mixtures into their constituent stereoisomers, for example, using HPLC on a chiral column, such as Hypersil naphthyl urea, or using separation of salts of stereoisomers. Compounds of the invention can be isolated in association with solvent molecules by crystallization from, or evaporation of, an appropriate solvent.

The pharmaceutically acceptable acid addition salts of the compounds of formula (I) that contain a basic center can be prepared in a conventional manner. For example, a solution of the free base can be treated with a suitable acid, either neat or in a suitable solution, and the resulting salt isolated either by filtration or by evaporation under vacuum of the reaction solvent. Pharmaceutically acceptable base addition salts can be obtained in an analogous manner by treating a solution of a compound of formula (I) with a suitable base. Both types of salt can be formed or interconverted using ion-exchange resin techniques. Thus, according to a further aspect of the invention, a method for preparing a compound of formula (I) or a salt or solvate (e.g., hydrate) is provided, followed by (i) salt formation, or (ii) solvate (e.g., hydrate) formation.

The following abbreviations are used hereafter in the accompanying examples: rt (room temperature), min (minute), h (hour), g (gram), mmol (millimole), m.p. (melting point), eq (equivalents), L (liter), mL (milliliter), μL (microliters), DMSO (dimethyl sulfoxide), $CH_2Cl_2$ (dichloromethane), MeOH (methanol), $Et_3N$ (triethylamine), EtOAc (ethyl acetate), ACOH (acetic acid), HCl (hydrochloric acid), $H_2S$ (hydrogen sulfide), aq (aqueous), NaOH (sodium hydroxide), t-Bu (tertiary butyl), NaCl (sodium chloride), $MgSO_4$ (magnesium sulfate), and THF (tetrahydrofuran).

The following illustrates specific examples of compounds of structural formula (I) and synthetic routes to some of these structures.

PREPARATION OF EXAMPLE 1

(3aR,10R)-(+)-10-Benzo[1,3]dioxol-5-yl-3a,4,9,10-tetrahydro-2-oxa-9,10a-diaza-cyclopenta[β]fluorene-1,3-dione

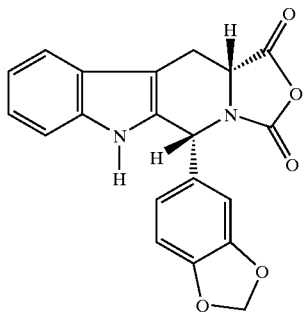

Example 1 can be prepared using the following synthetic sequence.

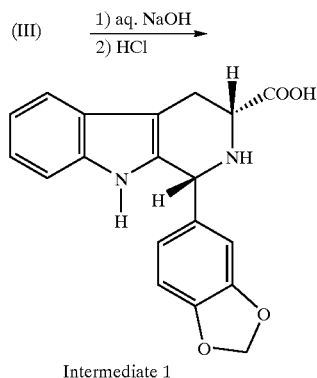

The addition of phosgene (COCl$_2$) to homoproline is described in S. H. Reich et al., *J. Med. Chem.*, 39, pp. 2781–2794 (1996).

Example 1 was prepared by the following alternative method. A suspension of Intermediate 1 (1.0 g, 3.0 mmol), Et$_3$N (1.0 mL, 7.1 mmol, 2.5 eq) and THF (25 mL) was immersed in a sonicator until all solid particles dissolved. Triphosgene (800 mg, 2.7 mmol) was added and the resulting suspension was stirred for 18 hours. A colorless solid was removed by filtration. The filtrate was concentrated and the crude residue was purified by chromatography (silica gel, 30% ethyl acetate: 70% hexanes) to provide 602 mg (55%) of Example 1 as a solid. mp 197–202° C. $^1$H NMR (DMSO-d$_6$) δ: 10.7 (s, 1H), 7.55–6.35 (m, 7H), 6.0 (d, J=15 Hz, 2H), 5.8 (s, 1H), 4.9 (dd, J=5.11 Hz, 1H), 3.3 (m, 2H); MS FD m/e 362 (p).

PREPARATION OF EXAMPLE 2

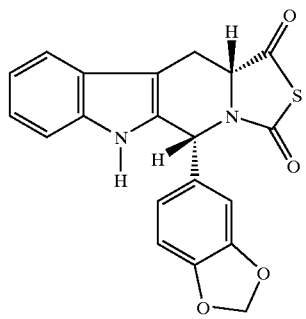

Example 2 was prepared using the following synthetic sequence.

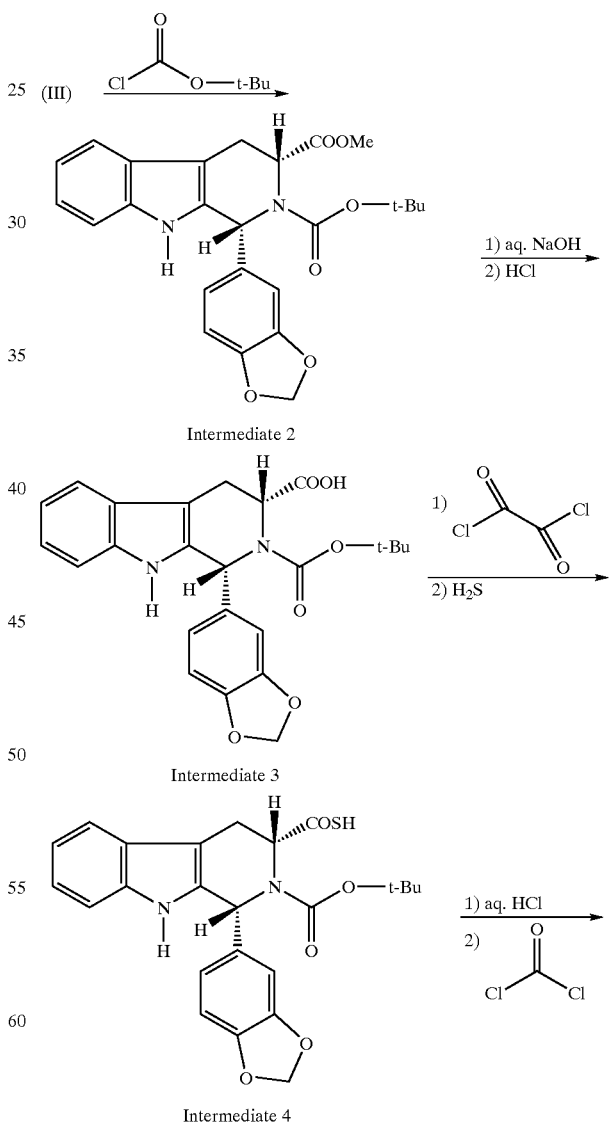

PREPARATION OF EXAMPLE 3

(3aR,10R)-10-Benzo[1,3]dioxol-5-yl-1-thioxo3a,4,9,10-tetrahydro-2-oxa-9,10a-diaza-cyclopenta[β]fluoren-3-one

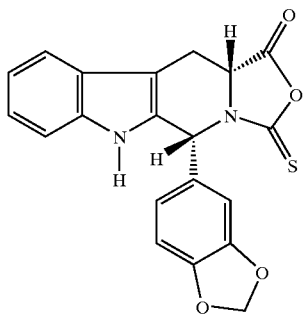

Example 3 was prepared by the following synthetic schemes.

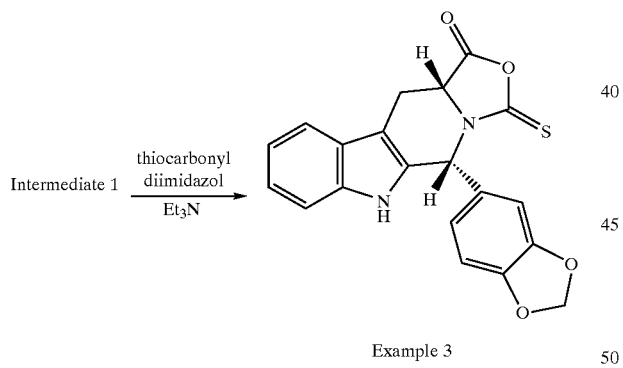

Triethylamine (0.39 mL, 2.98 mmol) was added to a stirred mixture of Intermediate 1 (1 g, 2.7 mmol) and thiocarbonyl diimidazole (0.57 g, 3.2 mmol) in $CH_2Cl_2$ (15 mL) at room temperature. The resulting slurry was stirred for 18 hours at room temperature. The resulting solution was concentrated in vacuo. Chromatography (silica gel, hexanes to 6:4 methylene chloride:hexanes) of the residue provided 0.33 g (32%) of Example 3 as a cream solid: 129–132° C. $^1$H NMR (DMSO-$d_6$) δ: 10.9 (s, 1H), 7.55 (d, J=7.68 Hz, 1H), 7.30 (d, J=7.68 Hz, 1H), 7.01–7.14 (m, 2H), 6.8–6.9 (m, 2H), 6.49 (s, 1H), 6.01 (s, 1H), 5.10 (dd, J=5.12, 10.98 Hz, 1H), 3.42 (dd, J=5.12, 15 Hz, 1H), 3.32 (s, 3H), 3.10 (dd, J=1.46, 15.00 Hz, 1H), 2.48–2.52 (m, 1H); IR (CHCl$_3$, cm$^{-1}$): 1735, 1691; MS FD m/e 378 (m+).

Example 3 also can be prepared by the following synthetic sequence:

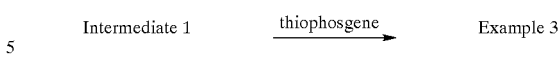

PREPARATION OF EXAMPLE 4

Example 4 is prepared from Example 1 by the following reaction.

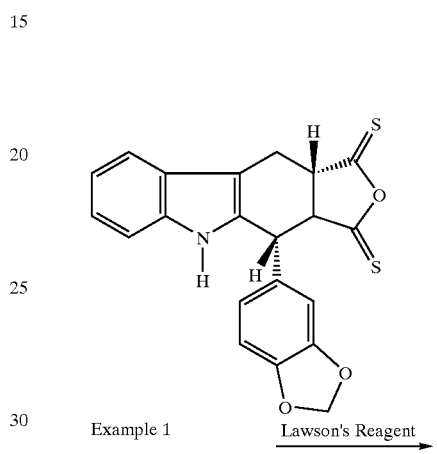

A general review of Lawesson's reagent can be found in M. P. Cava et al., *Tetrahedron*, 41, pp. 5061–5087 (1985).

PREPARATION OF EXAMPLE 5

(3aS,10R)-10-Benzo(1,3)dioxol-5-yl-2-methyl-3-thioxo-2,3,3a,4,9,10-hexahydro-2,9,10a-triazacyclopenta[b]fluoren-1-one

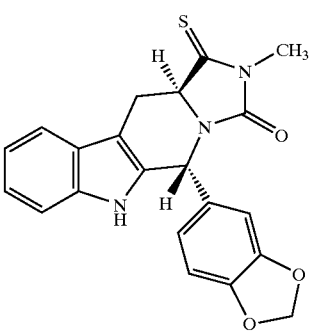

Example 5 is prepared from Intermediate 5 via a reaction with Lawesson's reagent. The synthesis of Intermediate 5 can be found in Daugan et al. U.S. Pat. No. 6,001,847.

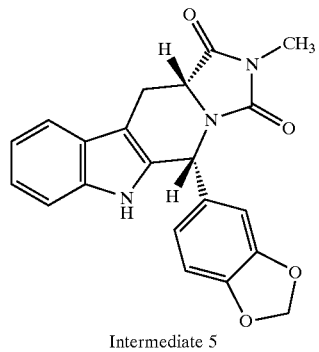

Intermediate 5

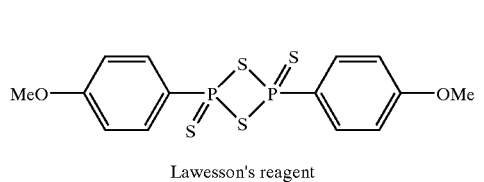

Lawesson's reagent

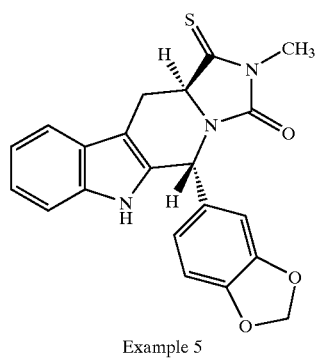

Example 5

Lawesson's reagent (0.43 g, 1.07 mmol) was added to a slurry of Intermediate 5 (0.40 g, 1.07 mmol) in anhydrous THF (25 mL). The mixture was stirred under a nitrogen blanket for 8 days at room temperature. LC/MS showed two peaks corresponding to Example 5, but only in 5–10% yield. The reaction mixture was concentrated in vacuo and was taken up in toluene. An additional 80 mg of Lawesson's reagent was added and the slurry was warmed to 80° C. for 4 hours. The reaction was cooled to room temperature, diluted with EtOAc (50 mL), and washed with saturated NaCl solution (20 mL). The organic layer was dried over $MgSO_4$, filtered, and concentrated in vacuo. The product was purified by column chromatography (silica gel, 0–5%) EtOAc/$CH_2Cl_2$) to provide an orange foam. Suspending the foam in MeOH and adding water gave a pale orange solid (112 mg, 26%) that was collected by filtration and dried in vacuo at 45° C.: mp 168–174° C.; TLC $R_f$ (100% $CH_2Cl_2$)= 0.60; $^1$H NMR (300 MHz, DMSO-$d_6$): δ 10.87 (s, 1H), 7.55 (d, J=7.6 Hz, 1H), 7.30 (d, J=7.9 Hz, 1H), 7.10 (td, J=7.4 Hz, J=1 Hz, 1H), 7.02 (td, J=7 Hz, J=0.9 Hz, 1H), 6.92–6.86 (m, J=7.3 Hz, 1H), 6.17 (s, 1H), 6.00 (s, 2H), 4.90 (dd, J=5.5 Hz, J=10.6 Hz, 1H), 3.56 (dd, J=5.5 Hz, J=15.0 Hz, 1H), 3.21 (s, 3H), 2.76 (ddd, J=1.1 Hz, J=10.8 Hz, J=14.5 Hz, 1H); $^{13}$C NMR (300 MHz, DMSO-$d_6$): δ 202.6, 153.7, 147.2, 136.8, 133.5, 131.2, 125.7, 121.7, 118.2, 111.4, 108.2, 106.5 101.2, 62.3, 52.8, 28.8, 26.6. MS (API) m/z 390 (M–H); $[\alpha]_D^{25°C.}$=−190.3° (c=0.21, DMSO). Anal. Calcd for $C_{21}H_{17}N_3O_3S \cdot 0.35H_2O$: C, 63.41; H, 4.49; N, 10.56; S, 8.06. Found: C, 63.44; H, 4.28; N, 10.48; S, 8.37. The relative stereochemistry of Example 5 was confirmed to be the trans isomer by NOE difference experiments (DMSO-$d_6$): no NOE enhancements from the C12a proton at 4.90 ppm to the C6 proton at 6.17 ppm and a positive enhancement with a C12 proton at 3.56 ppm.

PREPARATION OF EXAMPLE 6

(3aS,10R)-10-Benzo(1,3)dioxol-5-yl-2-methyl-1-thioxo-1,2,3a,4,9,10-hexahydro-2,9,10a-triazacyclopenta[b]fluoren-3-one

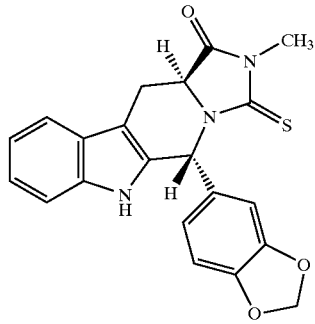

A mixture of Intermediate IIIa (4.00 g, 10.34 mmol) and 150 mL of THF was cooled to 0° C., then triethylamine (2.2 mL) was added giving a clear solution, momentarily followed by a new white precipitate. The solid was filtered, then washed with THF (2×20 mL). The filtrate was concentrated in vacuo to yield a white foam. The foam was taken up in methyl ethyl ketone (50 mL), then methyl thioisocyanate (0.94 g, 12.92 mmol) was added. The mixture was warmed to reflux for 5 hours. The reaction mixture was cooled to room temperature and the mixture was concentrated in vacuo. Purificaiton by flash chromatography on silica gel (0–3% EtOAc/$CH_2Cl_2$ and trituration with diethyl ether (2×10 mL) provided the product as a bright yellow solid (3.05 g, 75%): mp 234–236° C.; TLC $R_f$ (5% EtOAc/ $CH_2Cl_2$)=0.68; $^1$H NMR (300 MHz, DMSO-$d_6$): δ 10.97 (s, 1H), 7.54 (d, J=7.6 Hz, 1H), 7.30 (d, J=7.0 Hz, 1H), 7.10 (dt, J=7.3 Hz, J=0.9 Hz, 1H), 6.89–7.05 (m, 4H), 6.77 (s, 1H), 6.00 (d, J=1.2 Hz, 2H), 4.87 (dd, J=6.0 Hz, J=10.8 Hz, 1H), 3.43 (dd, J=6.1 Hz, J=15.1 Hz, 1H), 3.14 (s, 3H), 2.88–2.97 (m, 1H); MS (API) m/z 390 (M–H); $[\alpha]_D^{25°\ C.}=-410.25°$ (c=0.77, DMSO). Anal. Calcd for $C_{21}H_{17}N_3O_3S$: C, 64.43; H, 4.38; N, 10.73; S, 8.19. Found: C. 64.52; H, 4.49; N, 10.54; S, 8.36. The relative stereochemistry of Example 6 was confirmed to be the trans isomer by NOE difference experiments (DMSO-$D_6$): no NOE enhancements from the C3a proton at 4.87 ppm to the C10 proton at 6.77 ppm and a positive enhancement with benzene protons at 6.89–7.05 ppm.

PREPARATION OF EXAMPLE 6a

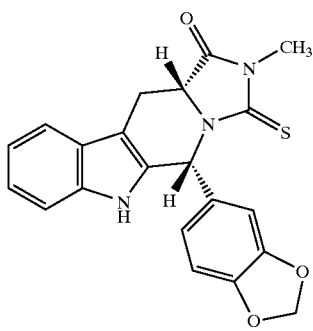

Example 6a was prepared in a manner identical to Example 6 using the appropriate stereoisomer of β-carboline hydrochloride, i.e., Intermediate III.

EXAMPLES 7–16

Examples 7–16 were prepared in a manner similar to Examples 1–6a.

EXAMPLE 7

(+–, trans)-2-Butyl-10-(4-methoxyphenyl)-1-thioxo-1,2,3a,4,9,10-hexahydro-2,9,10a-triazacyclopenta-[b]fluoren-3-one

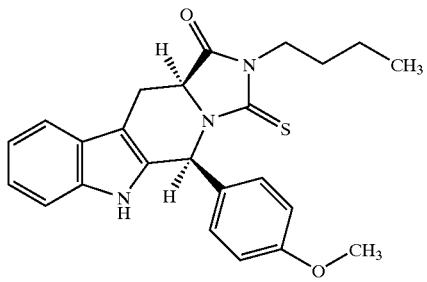

EXAMPLE 8

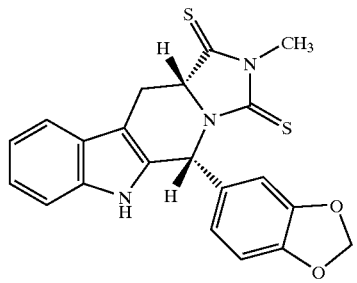

EXAMPLE 9

5-Benzo[1,3]dioxol-5-yl-5,6,11,11a-tetrahydroindolizino[6,7-b]indole-1,3-dione

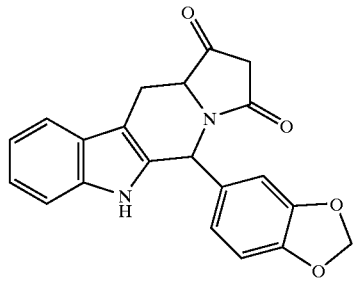

EXAMPLE 10

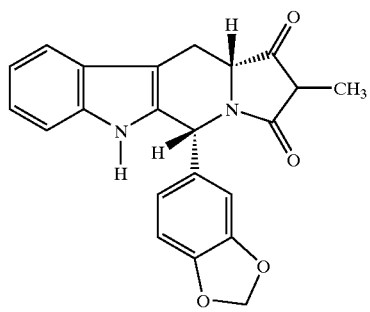

EXAMPLE 11

(+–, cis)-10-Benzo[1,3]dioxol-5-yl-2-methyl-2,3,3a,4,9,10-hexahydro-2,9,10a-triazacyclopenta[b]fluoren-1-one

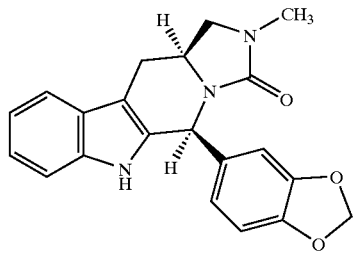

EXAMPLE 12

(+−, cis)-2-Benzyl-10-(4-methoxyphenyl)-1,2,3a,4,9,10-hexahydro-2,9,10a-triazacyclopenta[b]fluoren-3-one

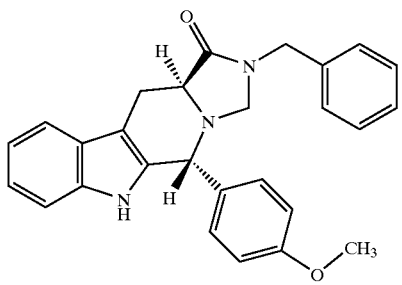

EXAMPLE 13

10-Benzo[1,3]dioxol-5-yl-3a,4,9,10-tetrahydro-3H-2-oxa-9,10a-diazacyclopenta[b]fluoren-1-one

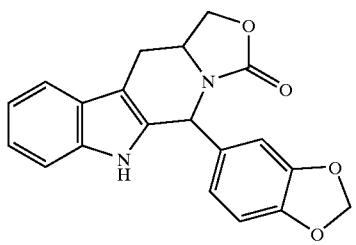

EXAMPLE 14

(+−, trans)-5-Benzo[1,3]dioxol-5-yl,2,3,5,6,11,11a-hexahydro-indolizino[6,7-b]indol-1-one

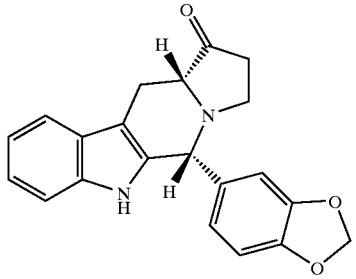

EXAMPLE 15

10-Benzo[1,3]dioxol-5-yl-3a,4,9,10-tetrahydro-3H-2-oxa-1-thia-9,10a-diazacyclopenta[b]fluorene-1-oxide

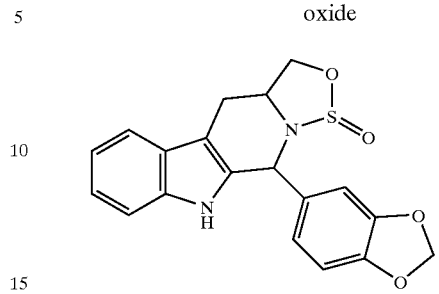

EXAMPLE 16

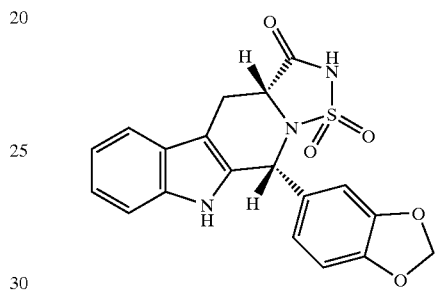

Compounds of the present invention can be formulated into tablets for oral administration. For example, a compound of formula (I) can be formed into a dispersion with a polymeric carrier by the coprecipitation method set forth in WO 96/38131, incorporated herein by reference. The coprecipitated dispersion then can be blended with excipients, then pressed into tablets, which optionally are film-coated.

The compounds of structural formula (I) were tested for an ability to inhibit PDE5. The ability of a compound to inhibit PDE5 activity is related to the $IC_{50}$ value for the compound, i.e., the concentration of inhibitor required for 50% inhibition of enzyme activity. The $IC_{50}$ value for compounds of structural formula (I) were determined using recombinant human PDE5.

The compounds of the present invention typically exhibit an $IC_{50}$ value against recombinant human PDE5 of less than about 50 $\mu$M, and preferably less than about 25 $\mu$M, and more preferably less than about 15 $\mu$m. The compounds of the present invention typically exhibit an $IC_{50}$ value against recombinant human PDE5 of less than about 1 $\mu$M, and often less than about 0.05 $\mu$M. To achieve the full advantage of the present invention, a present PDE5 inhibitor has an $IC_{50}$ of about 0.1 nM to about 15 $\mu$M.

The production of recombinant human PDEs and the $IC_{50}$ determinations can be accomplished by well-known methods in the art. Exemplary methods are described as follows:

Expression of Human PDEs

Expression in *Saccharomyces cerevisiae* (Yeast)

Recombinant production of human PDE1B, PDE2, PDE4A, PDE4B, PDE4C, PDE4D, PDE5, and PDE7 was carried out similarly to that described in Example 7 of U.S. Pat. No. 5,702,936, incorporated herein by reference, except that the yeast transformation vector employed, which is derived from the basic ADH2 plasmid described in Price et al., *Methods in Enzymology*, 185, pp. 308–318 (1990), incorporated yeast ADH2 promoter and terminator sequences and the *Saccharomyces cerevisiae* host was the protease-deficient strain BJ2-54 deposited on Aug. 31, 1998 with the American Type Culture Collection, Manassas, Va., under accession number ATCC 74465. Transformed host cells were grown in 2×SC-leu medium, pH 6.2, with trace metals, and vitamins. After 24 hours, YEP medium-containing glycerol was added to a final concentration of 2×YET/3% glycerol. Approximately 24 hr later, cells were harvested, washed, and stored at −70° C.

Human Phosphodiesterase Preparations

Phosphodiesterase Activity Determinations

Phosphodiesterase activity of the preparations was determined as follows. PDE assays utilizing a charcoal separation technique were performed essentially as described in Loughney et al. (1996). In this assay, PDE activity converts [32P]cAMP or [32P]cGMP to the corresponding [32P]5'-AMP or [32P]5'-GMP in proportion to the amount of PDE activity present. The [32P]5'-AMP or [32P]5'-GMP then was quantitatively converted to free [32P]phosphate and unlabeled adenosine or guanosine by the action of snake venom 5'-nucleotidase. Hence, the amount of [32P]phosphate liberated is proportional to enzyme activity. The assay was performed at 30° C. in a 100 μL reaction mixture containing (final concentrations) 40 mM Tris HCl (pH 8.0), 1 μM $ZnSO_4$, 5 mM $MgCl_2$, and 0.1 mg/mL bovine serum albumin (BSA). PDE enzyme was present in quantities that yield <30% total hydrolysis of substrate (linear assay conditions). The assay was initiated by addition of substrate (1 mM [32P]cAMP or cGMP), and the mixture was incubated for 12 minutes. Seventy-five (75) μg of Crotalus atrox venom then was added, and the incubation was continued for 3 minutes (15 minutes total). The reaction was stopped by addition of 200 μL of activated charcoal (25 mg/mL suspension in 0.1 M $NaH_2PO_4$, pH 4). After centrifugation (750×g for 3 minutes) to sediment the charcoal, a sample of the supernatant was taken for radioactivity determination in a scintillation counter and the PDE activity was calculated.

Purification of PDE5 from *S. cerevisiae*

Cell pellets (29 g) were thawed on ice with an equal volume of Lysis Buffer (25 mM Tris HCl, pH 8, 5 mM $MgCl_2$, 0.25 mM DTT, 1 mM benzamidine, and 10 μM $ZnSO_4$). Cells were lysed in a Microfluidizer® (Microfluidics Corp.) using nitrogen at 20,000 psi. The lysate was centrifuged and filtered through 0.45 μm disposable filters. The filtrate was applied to a 150 mL column of Q SEPHAROSE® Fast-Flow (Pharmacia). The column was washed with 1.5 volumes of Buffer A (20 mM Bis-Tris Propane, pH 6.8, 1 mM $MgCl_2$, 0.25 mM DTT, 10 μM $ZnSO_4$) and eluted with a step gradient of 125 mM NaCl in Buffer A followed by a linear gradient of 125–1000 mM NaCl in Buffer A. Active fractions from the linear gradient were applied to a 180 mL hydroxyapatite column in Buffer B (20 mM Bis-Tris Propane (pH 6.8), 1 mM $MgCl_2$, 0.25 mM DTT, 10 μM $ZnSO_4$, and 250 mM KCl). After loading, the column was washed with 2 volumes of Buffer B and eluted with a linear gradient of 0–125 mM potassium phosphate in Buffer B. Active fractions were pooled, precipitated with 60% ammonium sulfate, and resuspended in Buffer C (20 mM Bis-Tris Propane, pH 6.8, 125 mM NaCl, 0.5 mM DTT, and 10 μM $ZnSO_4$). The pool was applied to a 140 mL column of SEPHACRYL® S-300 HR and eluted with Buffer C. Active fractions were diluted to 50% glycerol and stored at −20° C.

The resultant preparations were about 85% pure by SDS-PAGE. These preparations had specific activities of about 3 μmol cGMP hydrolyzed per minute per milligram protein.

Inhibitory Effect on cGMP-PDE cGMP-PDE activity of compounds of the present invention was measured using a one-step assay adapted from Wells et al., *Biochim. Biophys. Acta*, 384, 430 (1975). The reaction medium contained 50 mM Tris-HCl, pH 7.5, 5 mM magnesium acetate, 250 μg/ml 5'-Nucleotidase, 1 mM EGTA, and 0.15 μM 8-[$H^3$]-cGMP. Unless otherwise indicated, the enzyme used was a human recombinant PDE5 (ICOS Corp., Bothell, Wash.).

Compounds of the invention were dissolved in DMSO finally present at 2% in the assay. The incubation time was 30 minutes during which the total substrate conversion did not exceed 30%.

The $IC_{50}$ values for the compounds examined were determined from concentration-response curves typically using concentrations ranging from 10 nM to 10 μM. Tests against other PDE enzymes using standard methodology showed that compounds of the invention are selective for the cGMP-specific PDE enzyme.

Biological Data

The compounds according to the present invention were typically found to exhibit an $IC_{50}$ value of less than 500 nM. An in vitro test data for representative compounds of the invention is given in the following table:

TABLE 1

In vitro results

| Example | PDE5 $IC_{50}$ (nM) |
|---|---|
| 1 | 205 |
| 3 | 53 |
| 5 | 12 |
| 6 | 12 |
| 7 | 20 |
| 9 | 200 |
| 11 | 60 |
| 12 | 60 |
| 13 | 70 |
| 14 | 390 |
| 15 | 20 |

Obviously, many modifications and variations of the invention as hereinbefore set forth can be made without departing from the spirit and scope thereof, and, therefore, only such limitations should be imposed as are indicated by the appended claims.

What is claimed is:

1. A compound having a formula

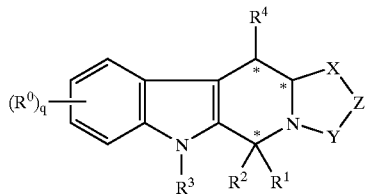

wherein $R^0$, independently, is selected from the group consisting of halo, $C_{1-6}$alkyl, aryl, heteroaryl, $C_{3-8}$cycloalkyl, $C_{3-8}$heterocycloalkyl, $C_{3-8}$cycloalkylQ, $C(\!=\!O)R^b$, $OC(\!=\!O)R^b$, $C(\!=\!O)OR^b$, $C_{1-4}$alkyleneNR$^b$R$^c$, $C_{1-4}$alkyleneHet, $C_{1-4}$alkyleneC$(\!=\!O)OR^b$, $C(\!=\!O)R^bSO_2R^d$, $C(\!=\!O)C_{1-4}$alkyleneHet, $C(\!=\!O)NR^bR^c$, $C(\!=\!O)NR^bR^d$, $C(\!=\!O)NR^b$ $C_{1-4}$alkyleneOR$^c$, $C(\!=\!O)NR^bC_{1-4}$alkyleneHet, $OR^b$, $OC_{1-4}$alkyleneC$(\!=\!O)OR^b$, $OC_{1-4}$alkyleneNR$^b$R$^c$, $OC_{1-4}$alkyleneHet, $OC_{1-4}$alkyleneOR$^b$, $OC_{1-4}$alkyleneNR$^b$C$(\!=\!O)OR^c$, $NR^bR^c$, $NR^bC_{1-4}$alkyleneNR$^b$R$^c$, $NR^bC(\!=\!O)RC$, $NR^bC(\!=\!O)$ $NR^bR^c$, $N(SO_2C_{1-4}alkyl)_2$, $NR^b(SO_2C_{1-4}alkyl)$, nitro, trifluoromethyl, trifluoromethoxy, cyano, $SO_2NR^bR^c$, $SO_2R^b$, $SOR^b$, $SR^b$, and $OSO_2CF_3$;

$R^1$ is selected from the group consisting of aryl optionally substituted with one or more substituent selected from the group consisting of halo, alkyl, hydroxyalkyl, alkoxy, alkoxyalkyl, haloalkyl, nitro, amino, alkylamino, acylamino, alkylthio, alkylsulfinyl, and alkylsulfonyl, heteroaryl optionally substituted with one or more substituent selected from the group consisting of halo, alkyl, hydroxy, hydroxyalkyl, alkoxy, alkoxyalkyl, haloalkyl, nitro, amino, alkylamino, acylamino, alkylthio, alkylsulfinyl, and alkylsulfonyl, a $C_{3-8}$cycloalkyl ring, a $C_{3-8}$heterocycloalkyl ring, a bicyclic ring

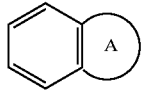

wherein the fused ring A is a 5- or 6-membered ring, saturated or partially or fully unsaturated, and comprises carbon atoms and optionally one to three heteroatoms selected from oxygen, sulfur, and nitrogen, hydrogen, arylC$_{1-3}$alkyl, C$_{1-3}$alkenylaryl, haloC$_{1-6}$alkyl, C$_{1-4}$alkyleneC$(\!=\!O\ OR^b$, C$_{1-4}$alkyleneC$(\!=\!O\ NR\ R^c$, C$_{3-9}$cycloalkyl, C$_{3-8}$cycloalkenyl, C$_{3-8}$heterocycloalkenyl, C$_{1-4}$alkyleneHet, C$_{1-4}$alkyleneQR$^b$, C$_{2-6}$alkenyleneQR$^b$, C$_{1-4}$alkyleneQC$_{1-4}$alkyleneQR$^b$,

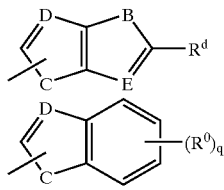

and a spiro substituent having the structure

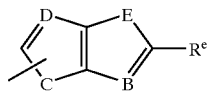

$R^2$ and $R^4$, independently, are selected from the group consisting of hydrogen, $C_{1-6}$alkyl, aryl, heteroaryl, arylC$_{1-3}$alkyl, C$_{1-3}$alkylenearyl, C$_{1-3}$alkyleneHet, C$_{3-8}$cycloalkyl, and C$_{3-8}$heterocycloalkyl;

$R^3$ is selected from the group consisting of hydrogen, $C_{1-6}$alkyl, $C_{3-8}$cycloalkyl, $C_{3-8}$heterocycloalkyl, $C_{2-6}$alkenyl, $C_{1-3}$alkylenearyl, arylC$_{1-3}$alkyl, $C(\!=\!O)R^b$, aryl, heteroaryl, $C(\!=\!O)R^b$, $C(\!=\!O)NR^bR^c$, $C(\!=\!O)$ $NR^bR^d$, $C(\!=\!S)NR^bR^c$, $C(\!=\!S)NR^bR^d$, $SO_2R^b$, $SO_2NR^bR^c$, $S(\!=\!O)R^b$, $S(\!=\!O)NR^bR^c$, $C(\!=\!O)NR^b$ $C_{1-4}$alkyleneOR$^b$, $C(\!=\!O)NR^bC_{1-4}$alkyleneHet, $C(\!=\!OC_{1-4}$alkylenearyl, $C(\!=\!O)$ $C_{1-4}$alkyleneheteroaryl, $C_{1-4}$alkylenearyl substituted with one or more of $SO_2NR^bR^c$, $NR^bR^c$, $C(\!=\!O)OR^b$, $NR^bSO_2CF_3$, $CN$, $NO_2$, $C(\!=\!O)R^b$, $OR^b$, $C_{1-4}$alkyleneNR$^b$R$^c$, and $OC_{1-4}$alkyleneNR$^b$R$^c$, $C_{1-4}$alkyleneheteroaryl, $C_{1-4}$alkyleneHet, $C_{1-4}$alkyleneC$(\!=\!O\ C_{1-4}$alkylenearyl, $C_{1-4}$alkyleneC$(\!=\!O\ C_{1-4}$alkyleneheteroaryl, $C_{1-4}$alkyleneC$(\!=\!O$ Het, $C_{1-4}$alkyleneC$(\!=\!O$ NR$^b$R$^c$, $C_{1-4}$alkyleneOR$^b$, $C_{1-4}$alkyleneNR$^b$C$(\!=\!O$ R$^b$, $C_{1-4}$alkylene $OC_{1-4}$alkyleneOR$^b$, $C_{1-4}$alkyleneNR$^b$R$^c$, $C_{1-4}$alkyleneC$(\!=\!O$ OR$^b$, and $C_{1-4}$alkylene $OC_{1-4}$alkyleneC$(\!=\!O)OR^b$;

X and Y, independently, are selected from the group consisting of $C(\!=\!O)$, SO, SO$_2$, $C(\!=\!S)$, and $C\!=\!C(R^a)_2$;

Z is O, X, or $C(R^a)_2$, or Z is NR$^d$ when X is SO, SO$_2$, $C(\!=\!S)$, or $C\!=\!C(R^a)_2$ or Y is SO or SO$_2$;

$R^a$, independently, is selected from the group consisting of hydrogen, $C_{1-10}$alkyl, $C_{2-10}$alkenyl, $C_{2-10}$alkynyl, aryl, heteroaryl, arylC$_{1-3}$alkyl, C$_{1-3}$alkylenearyl, $C(\!=\!O)OR^b$, $C(\!=\!O)NR^bR^d$, $C_{1-4}$alkyleneNR$^b$R$^c$, halo, NO$_2$, CF$_3$, CF$_3$O, OR$^b$, OC$(\!=\!O)R^b$, OC$_{1-4}$alkyleneC$(\!=\!O\ OR^b$, $C_{1-4}$alkyleneOC$_{1-4}$alkyleneC$(\!=\!O)OR^b$, $C(\!=\!O$ NR$^b$SO$_2$R$^d$, $C(\!=\!O)C_{1-4}$alkyleneHet, $C_{2-6}$alkenyleneNR$^b$R$^c$, $C(\!=\!O)NR^aC_{1-4}$alkyleneOR$^c$, $C(\!=\!O)NR^bC_{1-4}$alkyleneHet, OC$_{2-4}$alkyleneNR$^b$R$^c$, OC$_{1-4}$alkyleneCH(OR$^b$)CH$_2$NR$^b$R$^c$, OC$_{2-4}$alkyleneOR$^b$, OC$_{2-4}$alkyleneNR$^b$C$(\!=\!O)R^c$, NR$^b$R$^c$, NR$^b$C$_{1-4}$alkyleneNR$^b$R$^c$, NR$^b$C$(\!=\!O)R^c$, NR$^b$C$(\!=\!O)NR^bR^c$, N(SO$_2$C$_{1-4}$alkyl)$_2$, NR$^b$(SO$_2$ C$_{1-4}$alkyl), SO$_2$NR$^b$R$^c$, OSO$_2$trifluoromethyl, $C(\!=\!O)$ R$^b$, C$_{1-3}$alkyleneOR$^b$, CN, and C$_{1-6}$alkyleneC$(\!=\!O)$ OR$^b$;

$R^b$ is selected from the group consisting of hydrogen, C$_{1-6}$alkyl, aryl, arylC$_{1-3}$alkyl, C$_{1-3}$alkylenearyl, heteroaryl, heteroarylC$_{1-3}$alkyl, and C$_{1-3}$alkyleneheteroaryl;

$R^c$ is selected from the group consisting of hydrogen, C$_{1-6}$alkyl, C$_{3-8}$cycloalkyl, C$_{1-3}$alkyleneN(R$^b$)$_2$, aryl, arylC$_{1-3}$alkyl, C$_{1-3}$alkylenearyl, and heteroaryl;

$R^d$ is selected from the group consisting of hydrogen, C$_{1-6}$alkyl, aryl, heteroaryl, arylC$_{1-3}$alkyl, heteroaryl C$_{1-3}$alkyl, C$_{1-3}$alkyleneN(R$^a$)$_2$, C$_{1-6}$alkylenearyl, C$_{1-6}$alkyleneHet, haloC$_{1-6}$alkyl, C$_{3-8}$cycloalkyl, C$_{3-8}$heterocycloalkyl, C$_{1-3}$alkyleneHet,

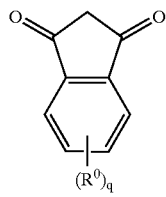

$C_{1-3}$alkyleneheteroaryl, $C_{1-6}$alkyleneC(=O)OR$^a$, and $C_{1-3}$alkyleneC$_{3-8}$heterocycloalkyl;

or R$^b$ and R$^d$ are taken together to form a 5- or 6-membered ring, optionally containing at least one heteroatom;

R$^a$ is null or is selected from the group consisting of hydrogen, $C_{1-6}$alkyl, aryl, heteroaryl, arylC$_{1-3}$alkyl, heteroarylC$_{1-3}$alkyl, $C_{1-3}$alkylenearyl, and $C_{1-3}$alkyleneheteroaryl;

Q is O, S, or NR$^b$;

B is O, S, or NR$^e$;

C is O, S, or NR$^b$;

D is CR$^b$ or N;

E is CR$^b$, C(R$^a$)$_2$, or NR$^e$;

Het represents a 5- or 6-membered heterocyclic ring, saturated or partially or fully unsaturated, containing at least one heteroatom selected from the group consisting of oxygen, nitrogen, and sulfur, and optionally substituted with $C_{1-4}$alkyl or C(=O)OR$^b$;

q is 0, 1, 2, 3, or 4; and pharmaceutically acceptable salts and hydrates thereof, wherein heteroaryl is a monocyclic or bicyclic ring system having one or two aromatic rings and five to ten atoms, with at least one nitrogen, oxygen, or sulfur atom in an aromatic ring, and wherein $C_{3-8}$heterocycloalkyl has one or more heteroatoms selected from the group consisting of oxygen, nitrogen, and sulfur.

2. The compound of claim 1 represented by the formula and pharmaceutically acceptable salts and solvates thereof.

3. The compound of claim 1 wherein q is 0.

4. The compound of claim 1 wherein R$^0$ is selected from the group consisting of aryl, Het, OR$^a$, C(=O)OR$^a$, $C_{1-4}$alkyleneNR$^a$R$^b$, OC(=O)R$^a$, C(=O)R$^a$, NR$^a$R$^b$, $C_{3-7}$cycloalkyl, $C_{3-7}$cycloalkylQ, C(=O)NR$^a$R$^b$, and C(=O)NR$^a$R$^c$, or two R$^0$ groups are taken together with the carbon atoms to which they are attached to form a 5- or 6-membered ring, saturated or partially or fully saturated, optionally substituted and optionally containing one or two heteroatoms selected from oxygen, nitrogen, and sulfur.

5. The compound of claim 1 wherein R$^1$ is selected from the group consisting of hydrogen, $C_{1-4}$alkyl, haloC$_{1-4}$alkyl, optionally substituted benzyl, $C_{3-6}$cycloalkylmethyl, pyridylC$_{1-3}$alkyl, and furylC$_{1-3}$alkyl.

6. The compound of claim 1 wherein R$^1$ is selected from the group consisting of CO$_{1-6}$alkyl, $C_{3-8}$cycloalkyl, $C_{3-6}$cycloalkenyl, $C_{1-4}$alkyleneQR$^a$, $C_{2-4}$alkenyleneQR$^a$, $C_{1-4}$alkyleneQC$_{1-4}$-alkyleneQR$^a$, wherein q is an integer 1 or 2, and G, independently, is C(R$^a$)$_2$, O, S, or NR$^a$.

7. The compound of claim 1 wherein R$^2$ is selected from the group consisting of each optionally substituted with halogen, $C_{1-3}$alkyl, OR$^a$, CO$_2$R$^a$, halomethyl, halomethoxy, cyano, nitro, and NR$^a$R$^b$.

8. The compound of claim 7 wherein R$^a$ is selected from the group consisting of hydrogen, $C_{1-6}$alkyl, and benzyl.

9. The compound of claim 1 wherein R$^2$ and R$^4$, independently, are selected from the group consisting of hydrogen, $C_{1-6}$alkyl, aryl, and heteroaryl.

10. The compound of claim 1 wherein R$^3$ is selected from the group consisting of benzimidazole, a triazole, imidazole, $C_{1-4}$alkyleneHet, wherein Het is selected from the group consisting of piperazine, morpholine, pyrrolidine, pyrrolidone, tetrahydrofuran, piperidine,

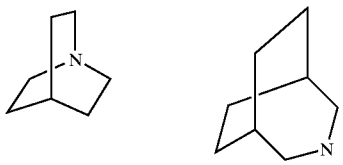

$C_{1-4}$alkylene$C_6H_5$, optionally substituted with one to three groups selected from the group consisting of $C(=O)OR^b$, $NR^bR^c$, $NR^bSO_2CF_3$, $SO_2NR^bR^c$, CN, $OR^b$, $C(=O)R^b$, $C_{1-4}$alkylene$NR^bR^c$, nitro, $OC_{1-4}$alkylenearyl, and $OC_{1-4}$alkylene$NR^bR^c$, $C_{1-4}$alkyleneC(=O)benzyl, $C_{1-4}$alkyleneC(=O)$OR^b$, $C_{1-4}$alkyleneC(=O)$NR^bR^c$, $C_{1-4}$alkyleneC(=O)$NR^bR^d$, $C_{1-4}$alkyleneHet, $NR^bR^c$, OH, $OC_{1-4}$alkyl, $C_6H_5$, $C_{1-4}$alkylene$NR^bR^c$, $C_{1-4}$alkylene$OR^b$, $C_{1-4}$alkyleneNHC(=O)$R^b$, and $C_{1-4}$alkylene$OC_{1-4}$alkylene$OR^b$.

11. The compound of claim 1 wherein —X-Z-Y— is selected from the group consisting of

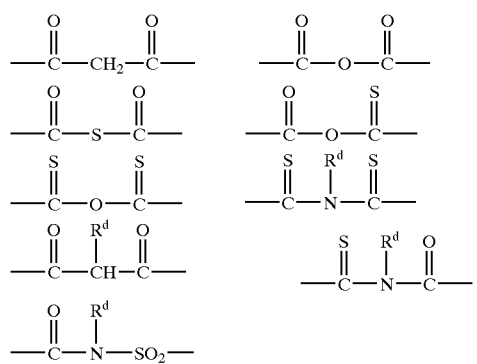

wherein $R^d$ is hydrogen, benzyl, or $C_{1-6}$ alkyl.

12. The compound of claim 1 wherein $R^1$ is selected from the group consisting of

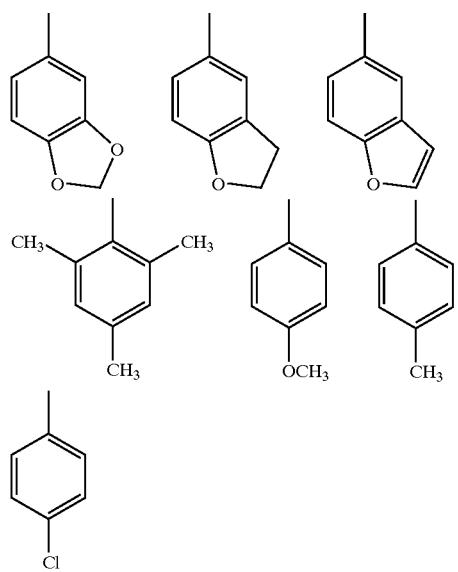

and $R^3$ is selected from the group consisting of hydrogen, $C_{1-6}$alkyl, C(=O)$NR^bR^d$, and $C_{1-4}$alkyleneHet; $R^2$ and $R^4$ are selected from the group consisting of hydrogen and $C_{1-6}$alkyl; and —X-Z-Y— is selected from the group consisting of

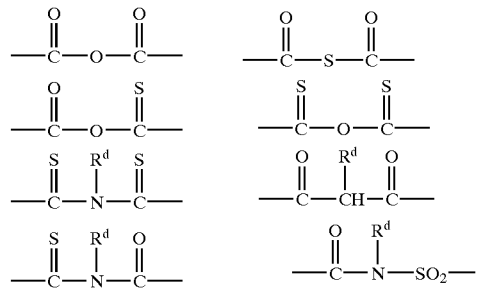

wherein $R^d$ is hydrogen, benzyl, or $C_{1-6}$alkyl.

13. A compound selected from the group consisting of

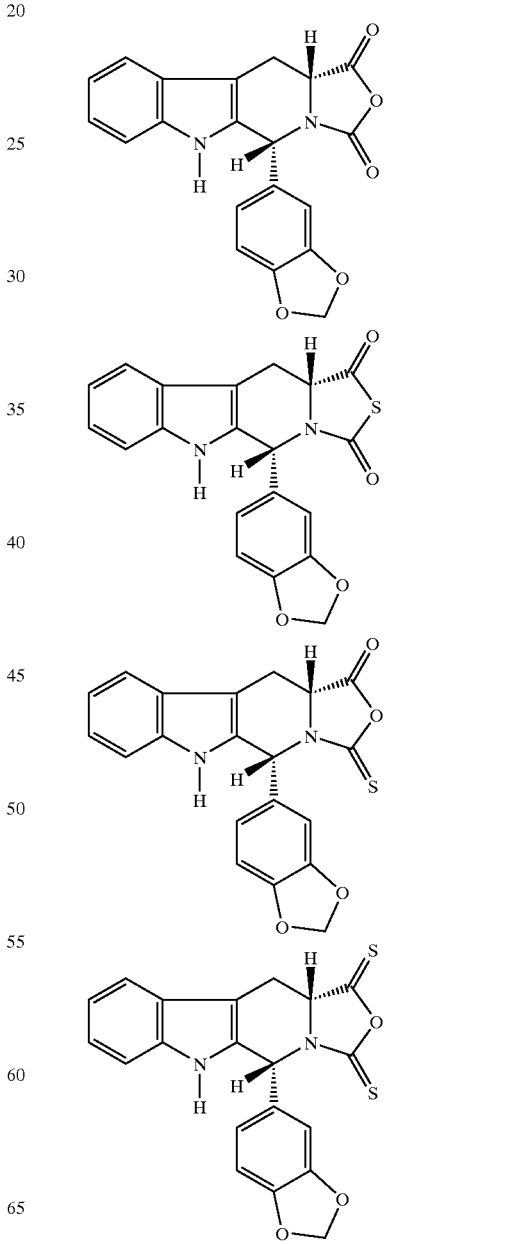

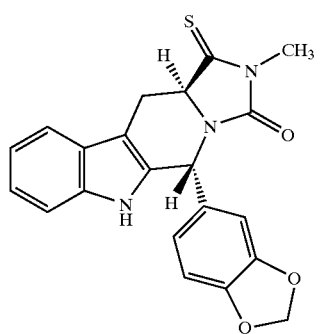
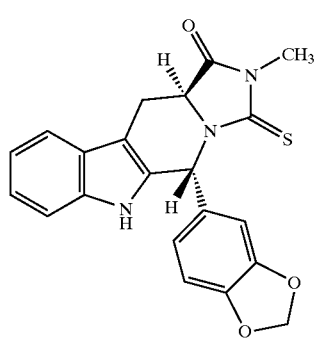
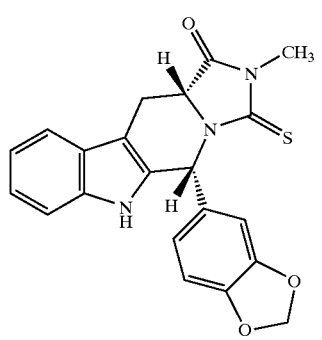
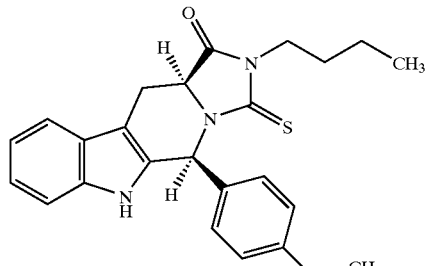
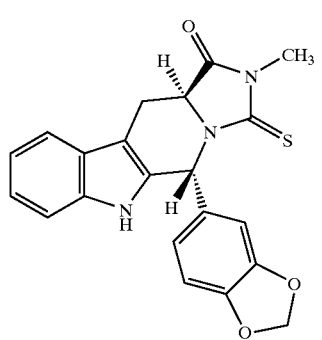
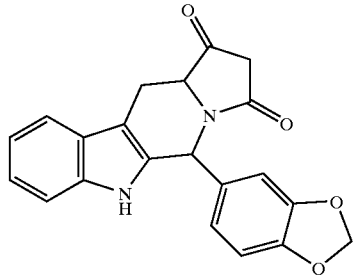
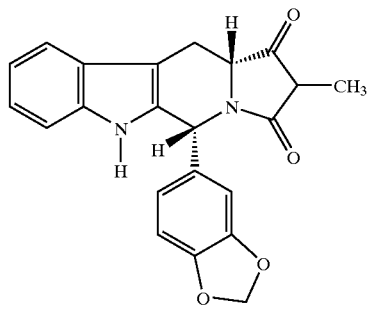
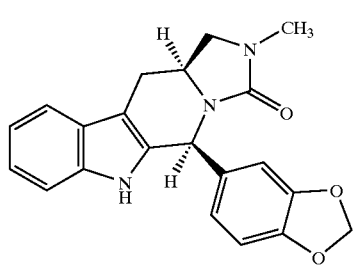
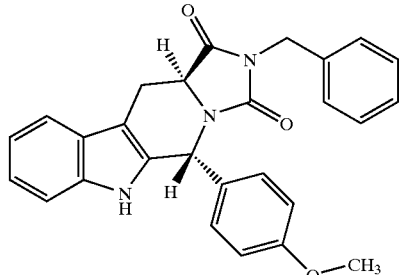
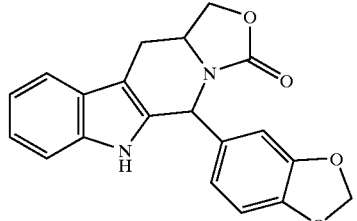
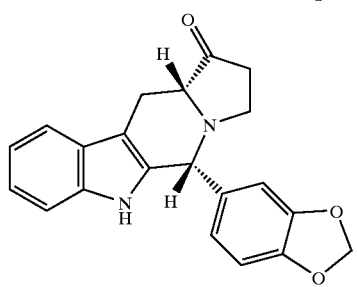

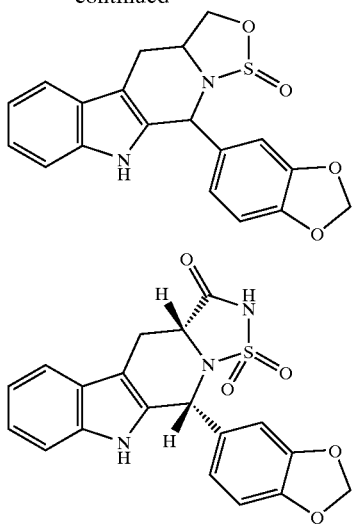

and pharmaceutically acceptable salts and solvates thereof.

14. A pharmaceutical composition comprising a compound of claim 1, together with a pharmaceutically acceptable diluent or carrier.

15. A method of treating a male mammal in the treatment of male erectile dysfunction comprising treating said male mammal with an effective amount of a pharmaceutical composition comprising a compound of claim 1, together with a pharmaceutically acceptable diluent or carrier.

16. The method of claim 15 wherein the treatment is an oral treatment.

17. A method of treating a female mammal in the treatment of female arousal disorder, comprising treating said female mammal with an effective dose of a composition comprising a compound of claim 1, together with a pharmaceutically acceptable diluent or carrier.

18. The method of claim 17 wherein the treatment is an oral treatment.

* * * * *

UNITED STATES PATENT AND TRADEMARK OFFICE
CERTIFICATE OF CORRECTION

PATENT NO.    : 6,858,620 B2
DATED         : February 22, 2005
INVENTOR(S)   : Mark W. Orme et al.

It is certified that error appears in the above-identified patent and that said Letters Patent is hereby corrected as shown below:

Title page,
Item [56], References Cited, OTHER PUBLICATIONS, "J.S. Madalengoitia et al.," reference, "vol. 5," should be -- Vol. 5, --.

Column 1,
Line 41, "$C_{3-8}$cyclo-alkylQ" should be -- $C_{3-8}$cycloalkylQ --.
Line 45, "$C(=O)NR^b$-$C_{1-4}$alkyleneOR$^c$," should be -- $C(=O)NR^bC_{1-4}$alkyleneOR$^c$, --.
Line 46, "$OC_{1-4}$-alkyleneC(=O)OR$^b$," should be -- $OC_{1-4}$alkyleneC(=O)OR$^b$, --.
Line 49, "$NR^b$-$C_{1-4}$alkyleneNR$^b$R$^c$," should be -- $NR^bC_{1-4}$alkyleneNR$^b$R$^c$, --.
Line 50, "$N(SO_2C_{1-4}$-alkyl$)_2$," should be -- $N(SO_2C_{1-4}$alkyl$)_2$, --.

Column 2,
Line 1, "$C_{1-3}$alkenyl-aryl," should be -- $C_{1-3}$alkenylaryl, --.
Line 2, "$C_{1-4}$alkylene-C(=O)NR$^b$R$^c$," should be -- $C_{1-4}$alkyleneC(=O)NR$^b$R$^c$, --.
Line 3, "$C_{3-8}$hetero-cycloalkeny 1," should be -- $C_{3-8}$heterocycloalkenyl, --.
Line 4, "$C_{2-6}$-alkyleneQR$^b$" should be -- $C_{2-6}$alkyleneQR$^b$ --.
Lines 31-32, "$N(SO_2C_{1-4}$-alkyl$)_2$," should be -- $N(SO_2C_{1-4}$alkyl$)_2$, --.
Lines 33-34, "C(=O)-NR$^b$R$^d$," should be -- C(=O)NR$^b$R$^d$, --.

Column 4,
Line 9, ""heteroaryl"," should be -- "heteroaryl" --.
Line 58, "C(=O)-OR$^a$" should be -- C(=O)(OR$^a$ --.
Line 61, "C(=O)-NR$^a$R$^c$," should be -- C(=O)NR$^a$R$^c$, --.

Column 14,
Line 60, "ACOH" should be -- AcOH --.

Column 15,
Line 35,
"

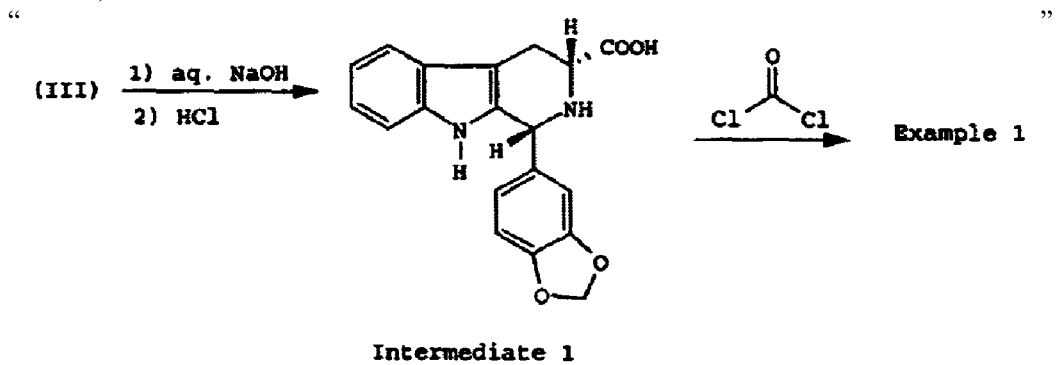

Intermediate 1

"

UNITED STATES PATENT AND TRADEMARK OFFICE
CERTIFICATE OF CORRECTION

PATENT NO. : 6,858,620 B2
DATED : February 22, 2005
INVENTOR(S) : Mark W. Orme et al.

It is certified that error appears in the above-identified patent and that said Letters Patent is hereby corrected as shown below:

Column 15 (cont'd),
should be
--

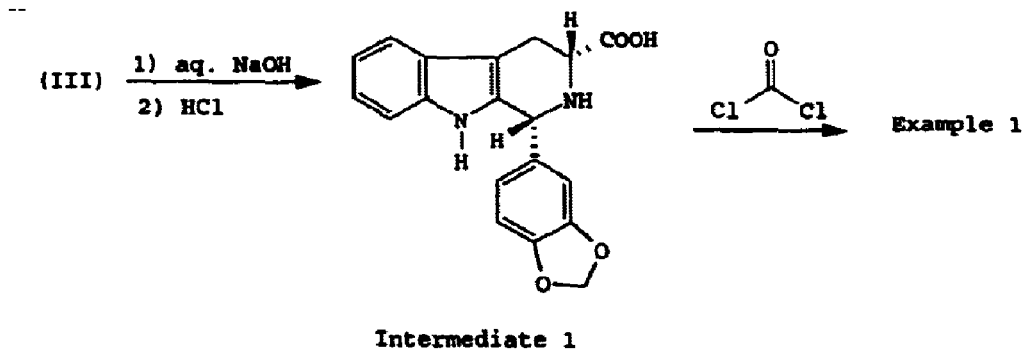

Column 17,
Line 4, "thioxo3" should be -- thioxo-3[a], --.
Lines 35-50,

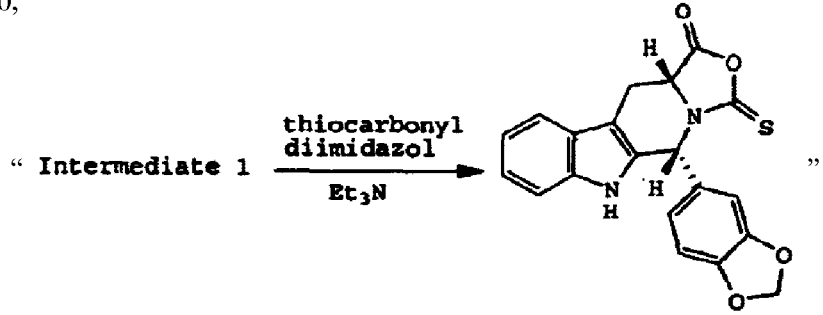

should be

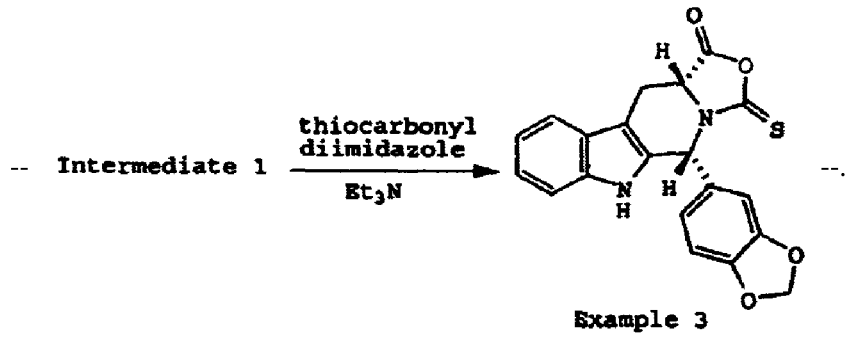

UNITED STATES PATENT AND TRADEMARK OFFICE
CERTIFICATE OF CORRECTION

PATENT NO.     : 6,858,620 B2
DATED          : February 22, 2005
INVENTOR(S)    : Mark W. Orme et al.

It is certified that error appears in the above-identified patent and that said Letters Patent is hereby corrected as shown below:

Column 18,
Line 31, "Lawson's" should be -- Lawesson's --.

Column 19,
Line 61, "$C_{21}H_{17}N_3O_3S.0.35H_2O$:" should be -- $C_{21}H_{17}N_3O_3S \cdot 0.35H_2O$: --.

Column 27,
Line 17, delete "$OC(=O)R^b$," second occurrence.
Line 19, "$C(=O)R^bSO_2R^d$," should be -- $C(=O)NR^bSO_2R^d$, --.
Line 25, "$NR^bC(=O)RC$" should be -- $NR^bC(=O)R^c$ --.
Line 54, "$C_{1-4}alkyleneC(=O)$ $OR^b$, $C_{1-4}alkyleneC(=O$ $NR$ $R^c$, $C_{3-9}cycloalkyl$," should be -- $C_{1-4}alkyleneC(=O)OR^b$, $C_{1-4}alkyleneC(=O)NR^bR^c$, $C_{3-8}cycloalkyl$, --.

Column 28,
Line 22, "$C(=OC_{1-4}alkylenearyl$," should be -- $C(=O)C_{1-4}alkylenearyl$, --.
Line 28, "$C_{1-4}alkyleneC(=O$ $C_{1-4}alkylenearyl$," should be
-- $C_{1-4}alkyleneC(=O)C_{1-4}alkyleneheteroaryl$, --.
Lines 28 and 29, "$C_{1-4}alkyleneC(=O$ $C_{1-4}alkyleneheteroa$ $ryl$," should be
-- $C_{1-4}alkyleneC(=O)C_{1-4}alkyleneheteroaryl$, --.
Line 29, "$C_{1-4}alkyleneC(=O$ $Het$," should be -- $C_{1-4}alkyleneC(=O)Het$, --.
Line 30, "$C_{1-4}alkyleneNR^bC(=O$ $NR^bR^c$," should be -- $C_{1-4}alkyleneNR^bC(=O)NR^bR^c$, --.
Line 31, "$C_{1-4}alkyleneNR^bC(=O$ $R^b$," should be -- $C_{1-4}alkyleneNR^bC(=O)R^b$, --.
Line 33, "$C_{1-4}alkyleneC(=O$ $OR^b$," should be -- $C_{1-4}alkyleneC(=O) OR^b$, --.
Lines 44 and 45, "$OC_{1-4}alkyleneC(=O$ $OR^b$," should be -- $OC_{1-4}alkyleneC(=O) OR^b$, --.
Line 46, "$C(=O$ $NR^bSO_2R$ $^d$," should be -- $C(=O)NR^bSO_2R^d$, --.

UNITED STATES PATENT AND TRADEMARK OFFICE
CERTIFICATE OF CORRECTION

PATENT NO. : 6,858,620 B2
DATED : February 22, 2005
INVENTOR(S) : Mark W. Orme et al.

It is certified that error appears in the above-identified patent and that said Letters Patent is hereby corrected as shown below:

Column 29,
Line 56, delete "$C_{1-4}$alkyl,".
Line 60, delete "$CO_{1-6}$alkyl,".

Signed and Sealed this

Eighth Day of November, 2005

JON W. DUDAS
*Director of the United States Patent and Trademark Office*